United States Patent
Newman et al.

(10) Patent No.: US 10,645,934 B2
(45) Date of Patent: May 12, 2020

(54) ENTEROBACTER SP-638 AND METHODS OF USE THEREOF

(75) Inventors: Lee Newman, Camillus, NY (US); Daniel van der Lelie, Chapel Hill, NC (US); Safiyh Taghavi, Chapel Hill, NC (US)

(73) Assignee: BROOKHAVEN SCIENCE ASSOCIATES/BROOKHAVEN NATIONAL LABORATORY, Upton, NY (US)

(*) Notice: Subject to any disclaimer, the term of this patent is extended or adjusted under 35 U.S.C. 154(b) by 275 days.

(21) Appl. No.: 13/634,135

(22) PCT Filed: Mar. 10, 2011

(86) PCT No.: PCT/US2011/027842
§ 371 (c)(1),
(2), (4) Date: Jan. 3, 2013

(87) PCT Pub. No.: WO2011/112781
PCT Pub. Date: Sep. 15, 2011

(65) Prior Publication Data
US 2013/0150240 A1 Jun. 13, 2013

Related U.S. Application Data

(60) Provisional application No. 61/313,415, filed on Mar. 12, 2010.

(51) Int. Cl.
*A01N 63/00* (2020.01)
*C12R 1/01* (2006.01)
*C12N 1/20* (2006.01)
*A01N 63/10* (2020.01)

(52) U.S. Cl.
CPC ............ *A01N 63/00* (2013.01); *A01N 63/10* (2020.01); *C12N 1/20* (2013.01); *C12R 1/01* (2013.01)

(58) Field of Classification Search
CPC ........ A01N 63/00; A01N 63/02; A01N 63/10; A01N 63/04; A01N 31/02; A01N 31/04; A01N 35/02; A01N 37/40; A01N 43/38; C12R 1/01; C12R 1/20
See application file for complete search history.

(56) References Cited

U.S. PATENT DOCUMENTS

2009/0105076 A1  4/2009  Stewart et al.

FOREIGN PATENT DOCUMENTS

WO   WO-2008/156380 A2 * 12/2008

OTHER PUBLICATIONS

Taghavi et al., Genome Survey and Characterization of Endophytic Bacteria Exhibiting a Beneficial Effect on Growth and Development of Poplar Trees, Dec. 5, 2008, Applied and Enviromental Microbiology, vol. 75 iss. 3, pp. 748-757.*
Aroca et al., Induction of Plant Tolerance to Semi-arid Environments by Beneficial Microorganisms—A Review, 2009, Sustainable Agriculture Reviews, pp. 121-135.*
Aroca et al., "Induction of Plant Tolerance to Semi-arid Environments by Beneficial Soil Microorganisms—A Review", Aug. 21, 2009, Springer, vol. 2, pp. 121-135.*
Holmes, A., et al., "Comparison of Two Multimetal Resistant Bacterial Strains: *Enterobacter* sp. YSU and *Stenotrophomonas maltophila* ORO2," *Current Microbiology*, vol. 59, No. 5, pp. 526-531, 2009.
Rogers, A., et al. "Inoculation of Hybrid Poplar with the Endophytic Bacterium *Enterobacter* sp. 638 Increases Biomass but does not Impact Leaf Level Physiology," *GCB Bioenergy*, vol. 4, pp. 364-370, 2012.
Saleh, S., et al., "Involvement of gacS and rpoS in enhancement of the plant growth-promoting capabilities of *Enterobacter cloacae* CAL2 and UW4," *Canadian Journal of Microbiology*, vol. 47, No. 8, pp. 698-705, 2001, [online] [Retrieved Dec. 20, 2013] from the internet <URL: http://www.nrcresearchpress.com/loi/cjm?open=2001#id_2001>.
Shah, S., et al., "Isolation and characterization of ACC deaminase genes from two different plant growth-promoting rhizobacteria," *Canadian Journal of Microbiology*, vol. 44, No. 9, pp. 833-843, 1998, [online] [Retrieved Dec. 20, 2013] from the internet <URL: http://www.nrcresearchpress.com/loi/cjm?open=2001#id_1998>.
Taghavi, S., et al., "Genome Sequence of the Plant Growth Promoting Endophytic Bacterium *Enterobacter* sp. 638," *PLOS Genetics*, vol. 6, Issue 5, pp. 1-15, 2010.
Wang, E., et al., "Diverse endophytic bacteria isolated from a leguminous tree *Conzattia multiflora* grown in Mexico," *Archives of Microbiology*, vol. 186, No. 4, pp. 251-259, 2006.
Asghar, H.N. et al., "Screening rhizobacteria for improving the growth, yield, and oil content of canola (*Brassica napus* L.)," Australian Journal of Agricultural Research, 2004; 55(2): p. 187-194.
Belimov, A.A. et al., "Cadmium-tolerant plant growth-promoting bacteria associated with the roots of Indian mustard (*Brassica juncea* L. Czern.)," Soil Biol. Biochem., 2005; 37: p. 241-250.
Bent, E. et al., "Alterations in plant growth and in root hormone levels of lodgepole pines inoculated with rhizobacteria," Can. J. Microbiol., 2001; 47: p. 793-800.

(Continued)

Primary Examiner — Ali Soroush
(74) Attorney, Agent, or Firm — Chainey P. Singleton; Ying-Horng Liu

(57) ABSTRACT

The present invention relates to a novel species of *Enterobacter*, *Enterobacter* sp. 638, and to its use in connection, for example, with a method for increasing growth in a plant, increasing biomass in a plant, increasing fruit and/or seed productivity in a plant, increasing disease tolerance and/or resistance in a plant, and increasing drought tolerance and/or resistance in a plant, as compared to a control or wild-type plant grown under identical conditions without application of the inventive method or composition. The methods include applying an effective amount of a composition, which includes an isolated culture of *Enterobacter* sp. 638, to the plant.

5 Claims, 7 Drawing Sheets

(56) References Cited

OTHER PUBLICATIONS

Figure 1:
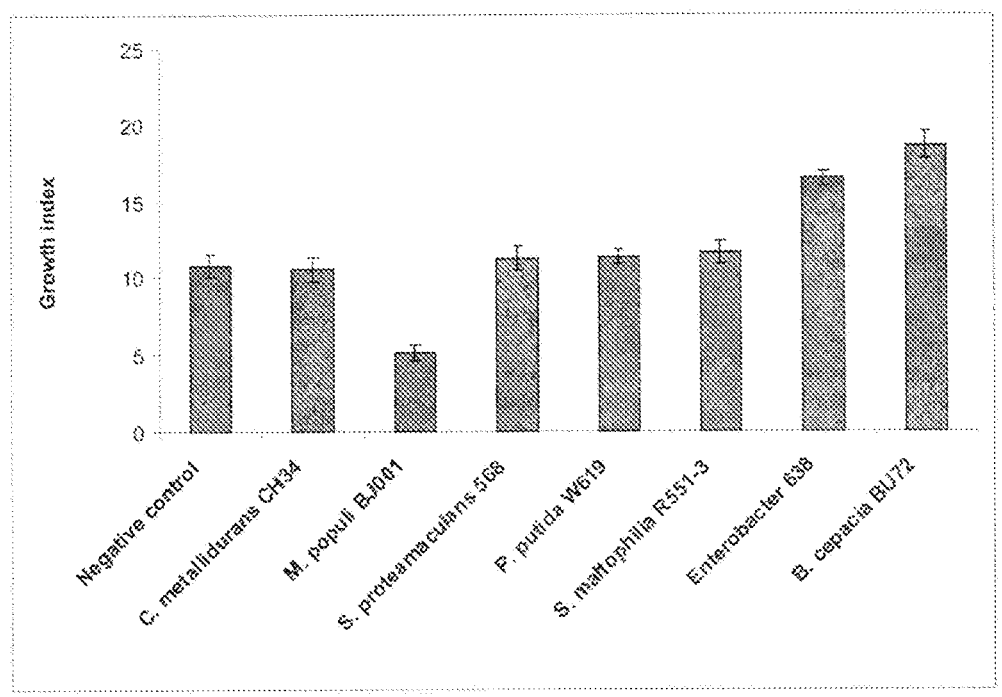

Bertagnolli, B.L. et al., "Extracellular enzyme profiles of the fungal pathogen *Rhizoctonia solani* isolate 2B-12 and of two antagonists, Bacillus megatherium strain B153-2-2 and Trichoderma harzianum isolate Th008. I. Possible correlations with inhibition of growth and biocontrol," Physiological and Molecular Plant Pathology, 1996; 48(3): p. 145-160.
Buyer, J. et al., "Iron Transport-mediated Antagonism between Plant Growth-promoting and Plant-deleterious Pseudomonas Strains," Journal of Biological Chemistry, 1986; 261(2): p. 791-794.
Buyer, J. et al., "Structure of Pseudobactin A214, a Siderophore from a Bean-Deleterious Pseudomonas," Biochemistry, 1986; 25(19): p. 5492-5499.
Cho, S.M. et al., "2R,3R-Butanediol, a Bacterial Volatile Produced by Pseudomonas chlororaphis O6, Is Involved in Induction of Systemic Tolerance to Drought in *Arabidopsis thaliana*," MPMI vol. 21, No. 8, 2008; p. 1067-1075.
Dell'Amico, E. et al., "Analysis of rhizobacterial communities in perennial Graminaceae from polluted water meadow soil, and screening of metal-resistant, potentially plant growth-promoting bacteria," FEMS Microbiology Ecology, 2005; 52(2): p. 153, 162.
Doty, S.L., "Enhancing phytoremediation through the use of transgenics and endophytes," New Phytologist, 2008; 179(2); p. 318-333.
Dowling, D.N. et al., "Metabolites of Pseudomonas involved in the biocontrol of plant disease," Trends in Biotechnology, 1994; 12(4): p. 133-141.
Garcia De Salamone, I.E. et al. "Cytokinin production by plant growth promoting rhizobacteria and selected mutants," Canadian Journal of Microbiology, 2001; 47(5): p. 404-411.
Goddijn, O. et al., "Sensing trehalose biosynthesis in plants," Plant Journal, 1998; 14(2): p. 143-146.
James, E.K., "Nitrogen fixation in endophytic and associative symbiosis," Field Crops Research, 2000; 65(2-3); p. 197-209.
Jeun, Y.C. et al., "Cytological observations of cucumber plants during induced resistance elicited by rhizobacteria," Biological Control, 2004; 29(1): p. 34-42.
Kloepper, J.W. et al., "Induced Systemic Resistance and Promotion of Plant Growth by *Bacillus* spp.," Phytopathology, 2004; 94(11): p. 1259-1266.
Krechel, A. et al., "Potato-associated bacteria and their antagonistic potential towards plant-pathogenic fungi and the plant-parasitic nematode Meloidogyne incognito (Kofoid & White) Chitwood," Canadian Journal of Microbiology, 2002; 48(9): p. 772-786.
O'Sullivan, D. et al., "Traits of Fluorescent *Pseudomonas* spp. Involved in Suppression of Plant Root Pathogens," Microbiological Reviews, 1992. 56(4): p. 662-676.
Ramos-Gonzales, M.I. et al., "Analysis of Pseudomonas putida KT2440 Gene Expression in the Maize Rhizosphere: In Vitro Expression Technology Capture and Identification of Root-Activated Promoters," Journal of Bacteriology, 2005; 187(12): p. 4033-4041.
Ryan, R.P. et al., "The versatility and adaptation of bacteria from the genus *Stenotrophomonas*," Nature Reviews Microbiology, 2009; 7(7): p. 514-525.
Ryu, C.M. et al., "Plant growth-promoting rhizobacteria systemically protect *Arabidopsis thaliana* against Cucumber mosaic virus by a salicylic acid and NPR1-independent and jasmonic acid-dependent signaling pathway," Plant Journal, 2004; 39(3): p. 381-392.
Spencer, M. et al., "Induced defence in tobacco by Pseudomonas chlororaphis strain O6 involves at least the ethylene pathway," Physiological and Molecular Plant Pathology, 2003; 63(1): p. 27-34.
Taghavi, S. et al., "Genome Survey and Characterization of Endophytic Bacteria Exhibiting a Beneficial Effect on Growth and Development of Poplar Trees," App Environ Microbiol, 2009 75(3): p. 748-757.
Van Loon, L.C. et al., "Systemic Resistant Induced by Rhizosphere Bacteria," Annual Review of Phytopathology, 1998; 36: p. 453-483.
Weyens, N. et al., "Colonization and plant growth promoting capacity of the endophyte Pseudomonas putida W619 after inoculation in hybrid poplar," FEMS Microbiol. Ecol., 2009; submitted for publication (not attached).
Zhang, S. et al., "Tobacco growth enhancement and blue mold disease protection by rhizobacteria: Relationship between plant growth promotion and systemic disease protection by PGPR strain 90-166," Plant and Soil, 2004; 262 (1-2): p. 277-288.
Weyens, N. et al., "Exploiting plant-microbe partnerships to improve biomass production and remediation", Trends in Biotechnology, Elsevier Publications, Cambridge, GB, vol. 27, No. 10, pp. 591-598 (not attached).

\* cited by examiner

ENTEROBACTER SP-638 AND METHODS OF USE THEREOF

CROSS-REFERENCE TO RELATED APPLICATION

This application is a U.S. National Phase of, and Applicants claim priority from, International Application No. PCT/US11/27842 filed on Mar. 10, 2011, which claims benefit of U.S. Provisional Application Ser. No. 61/313,415 filed on Mar. 12, 2010, which is incorporated herein by reference in its entirety.

This invention was made with Government support under contract number DE-AC02-98CH10886, awarded by the U.S. Department of Energy. The Government has certain rights in the invention.

BACKGROUND OF THE INVENTION

The present invention relates to a novel species of *Enterobacter*, and to its use in connection with, among other things, plant growth and development.

Changes in the Earth's climate can be expected to have a strong effect on agricultural productivity. For example, increases in emissions from fossil fuel combustion are considered to have affected the Earth's climate, which have made the production of biofuels from renewable resources more desirable. Another way in which climate change is expected to impact agricultural productivity is by increasing temperatures and by affecting rainfall patterns.

Although an increased demand of agricultural resources in the production of feedstocks for biofuel production is desirable, this increased demand is balanced by a simultaneous increased demand for food to feed a still growing world population.

Therefore, there is a need for sustainable practices that can be used to optimize the production of food and biofuel feedstocks. Such practices would optimally increase overall plant productivity in a sustainable manner, increase drought tolerance in plants so that crops and feedstocks can withstand major fluctuations in rainfall patterns, and increase tolerance to pathogen infections in plants.

SUMMARY OF THE INVENTION

In one aspect, the invention relates to an isolated culture of *Enterobacter* sp. 638.

In another aspect, the invention relates to an inoculant for a plant. The inoculant includes an isolated culture of *Enterobacter* sp. 638 and a biologically acceptable medium.

In yet another aspect, the invention relates to a method for increasing growth in a plant. The method includes applying a composition to the plant in an amount effective for increasing growth in the plant, wherein the composition includes an isolated culture of *Enterobacter* sp. 638.

In a further aspect, the invention relates to a method for increasing biomass in a plant. The method includes applying a composition to the plant in an amount effective for increasing biomass in the plant. The composition includes an isolated culture of *Enterobacter* sp. 638.

In yet a further aspect, the invention relates to a method for increasing fruit and/or seed productivity in a plant. The method includes applying a composition to the plant in an amount effective for increasing fruit and/or seed productivity in the plant. The composition includes an isolated culture of *Enterobacter* sp. 638.

In an additional aspect, the invention relates to a method for increasing disease tolerance in a plant. The method includes applying a composition to the plant in an amount effective for increasing disease tolerance in the plant. The composition includes an isolated culture of *Enterobacter* sp. 638.

In yet an additional aspect, the invention relates to a method of increasing drought tolerance in a plant. The method includes applying a composition to the plant in an amount effective for increasing disease tolerance in the plant. The composition includes an isolated culture of *Enterobacter* sp. 638.

Other objects advantages and aspects of the present invention will become apparent from the following specification and the figures.

BRIEF DESCRIPTION OF THE DRAWING(S)

FIG. 1 depicts growth indexes for poplar cuttings inoculated with different endophytic bacteria. Growth indexes were determined 10 weeks after the inoculating and planting of the cuttings in sandy soil. Per condition, seven plants were used. Plants were grown in the greenhouse. Non-inoculated plants were used as references. Bars indicate standard errors. Growth indexes were calculated as (Mt−MO)/MO after 10 weeks of growth of inoculated and non-inoculated plants. MO, plant's weight (g) at week 0; Mt, plant's weight (g) after 10 weeks. The statistical significance of the increased biomass production of inoculated plants, compared to that of non-inoculated control plants, was confirmed at the 5% level (**) using the Dunnett test.

Figure 2:
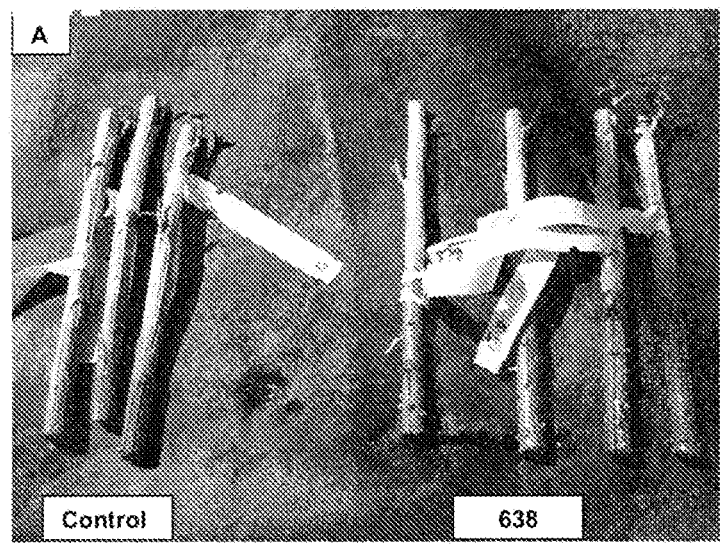
Figure 2:
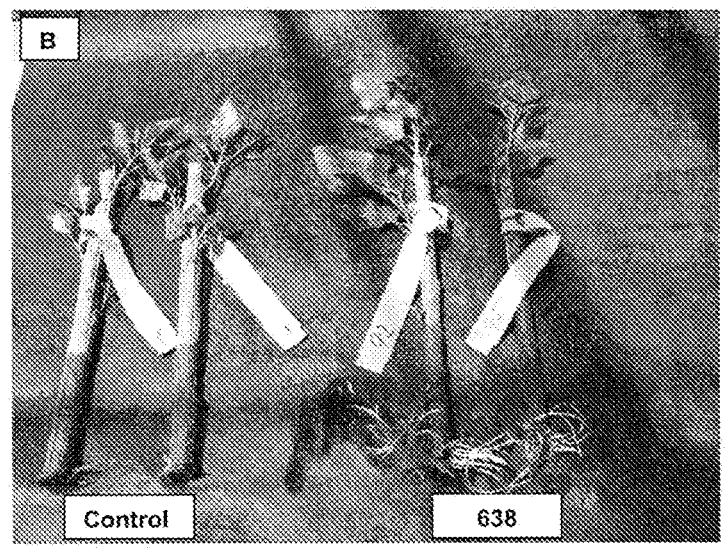

FIG. 2 shows the effects of *Enterobacter* sp. 638 on the shoot and root formation of poplar DN-34. Plants were incubated hydroponically in half-strength Hoagland's solution in the absence (Control) or presence (638) of strain 638. Root and shoot development are presented after 1 (A) and 10 (B) weeks.

Figure 3:
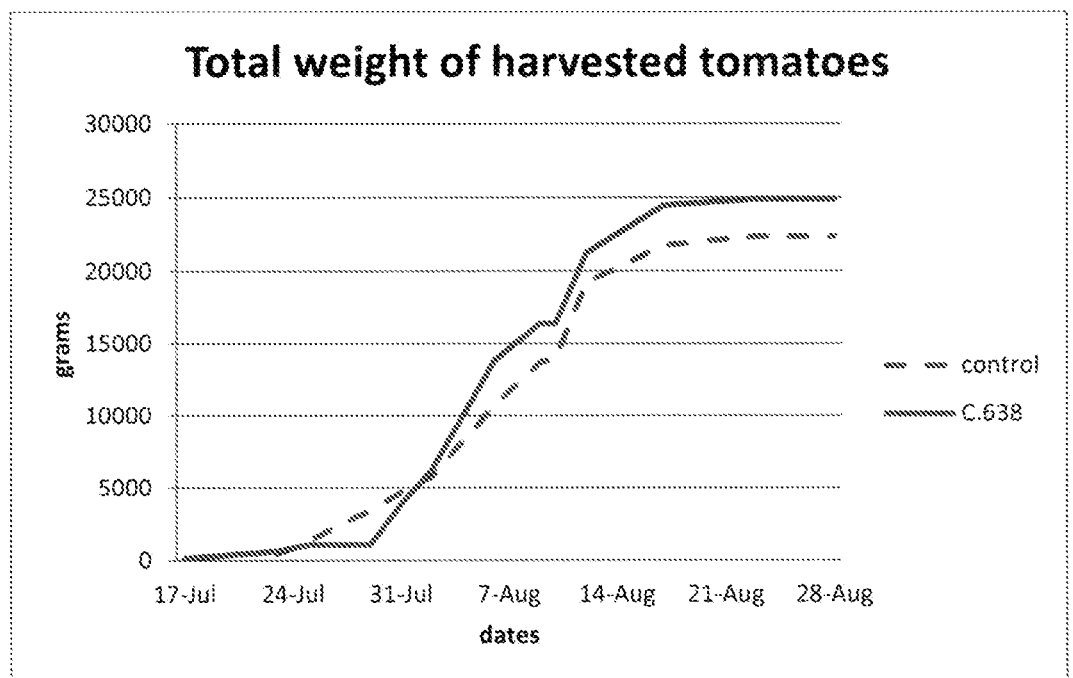

FIG. 3 shows the total weight of harvested tomatoes over a 4 month growing period. Plants inoculated with *Enterobacter* sp. 638 had a 10% higher yield as compared to non-inoculated control plants.

Figure 4:
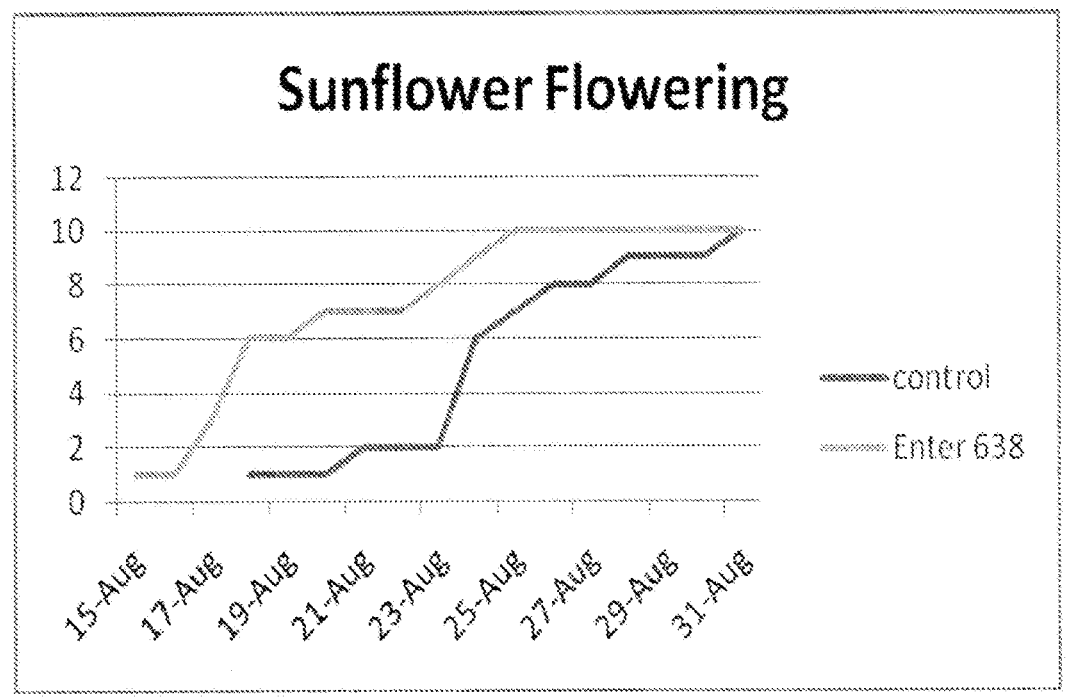

FIG. 4 presents a decrease in time to flowering of sunflower plant inoculated with *Enterobacter* sp. 638 as compared to non-inoculated sunflower plant as controls.

Figure 5:
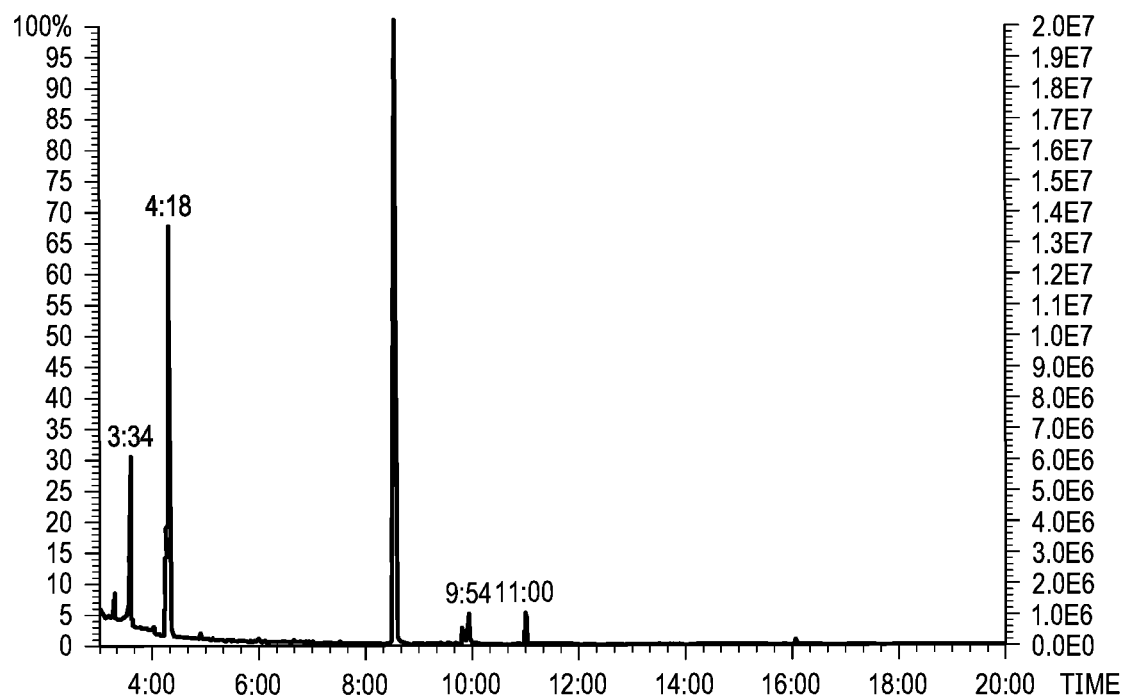
Figure 5:
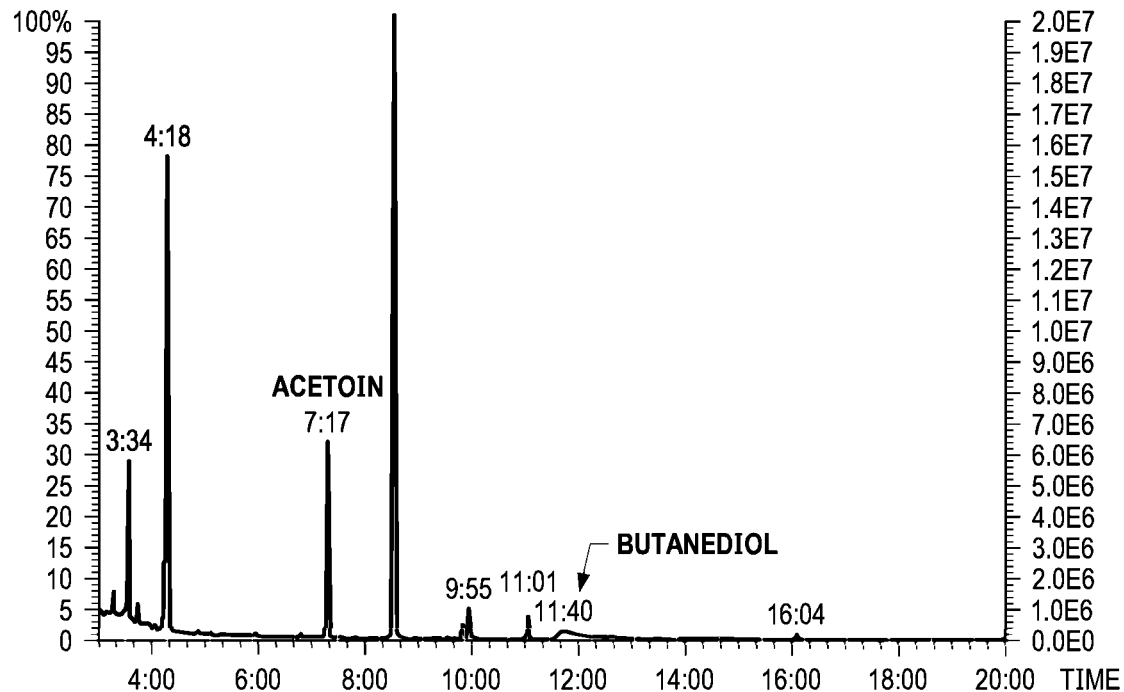

FIG. 5 shows a comparison of chromatographs of *Enterobacter* sp. 638 extracts grown in the absence (top chromatograph) or presence (bottom chromatograph) of plant extracts. Note the production of Acetoin and 2,3-Butanediol in the presence of plant extracts. This result was confirmed in a defined medium containing sucrose.

Figure 6:
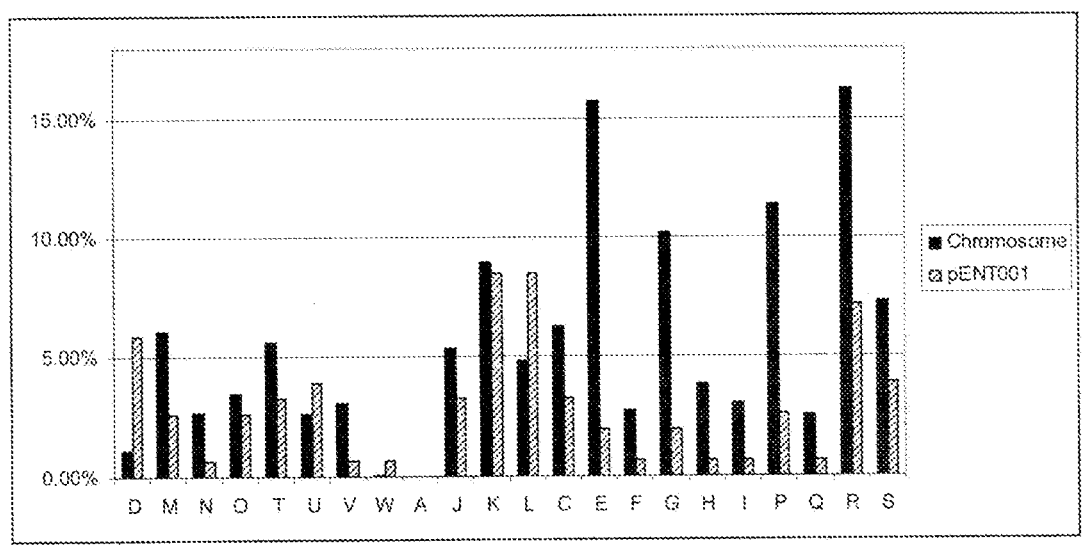

FIG. 6 shows percentage of gene from a particular COG class depending of their genetic localization: chromosome or plasmid pENT638-1. Legend of the. Cog class: D: Cell cycle control, cell division, chromosome partitioning; M Cell wall/membrane/envelope biogenesis; N Cell motility; 0 Posttranslational modification, protein turnover, chaperones; T Signal transduction mechanisms; U Intracellular trafficking, secretion, and vesicular transport; V Defense mechanisms; W Extracellular structures; J Translation, ribosomal structure and biogenesis; K Transcription; L Replication, recombination and repair; C Energy production and conversion; E Amino acid transport and metabolism; F Nucleotide transport and metabolism; G Carbohydrate transport and metabolism; H Coenzyme transport and metabolism; I Lipid transport and metabolism; P Inorganic ion transport and metabolism; Q Secondary metabolites biosynthesis, transport and catabolism; R General function prediction only; S Function unknown.

Figure 7:
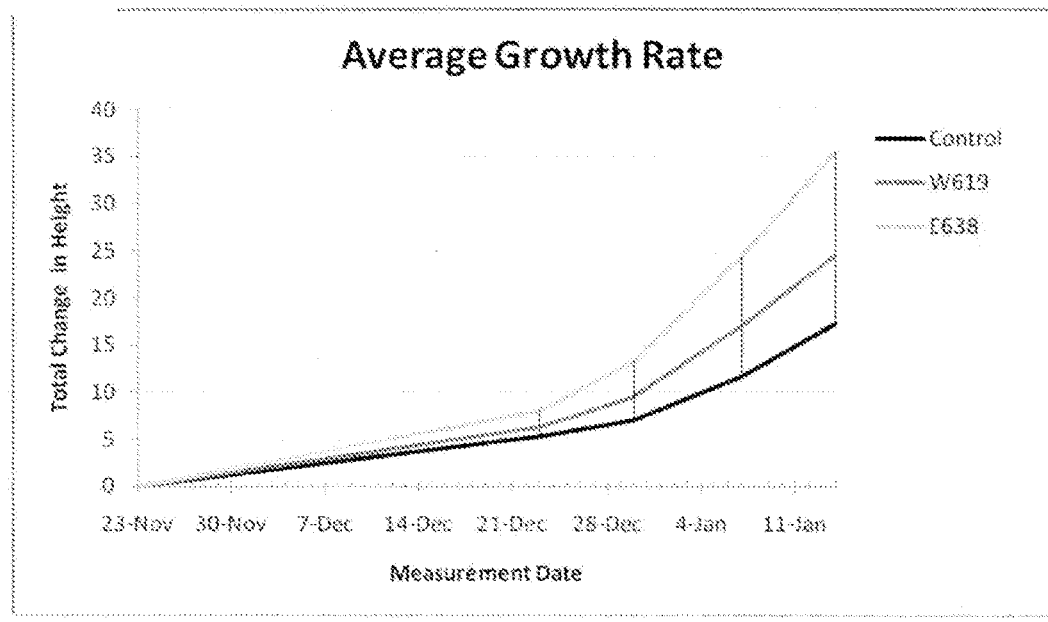
Figure 7:
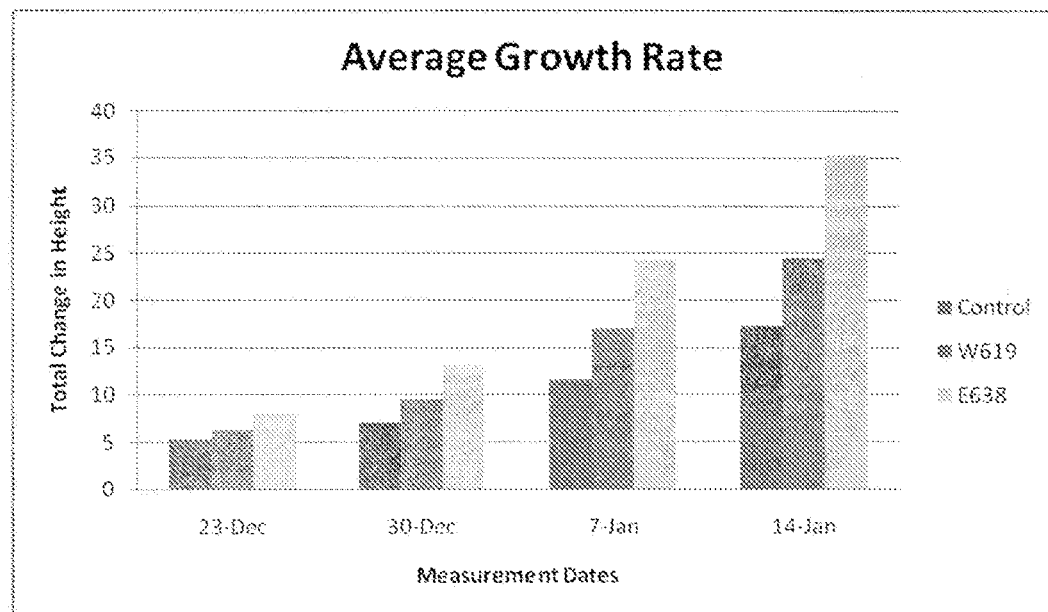

FIG. 7 shows increased biomass production of tobacco when inoculated with *Enterobacter* sp. 638. For comparison, non-inoculated control plants and plants inoculated with *Pseudomonas putida* W619 were included. For tobacco, not only did the plants inoculated with *Enterobacter* sp. 638 show the most increase growth, but also earlier onset of flowering as was seen with sunflower.

DETAILED DESCRIPTION OF THE INVENTION

A biological deposit of the *Enterobacter* sp. 638 according to the invention was made on Mar. 4, 2011 with ATCC Patent Depository, 10801 University Blvd., Manassas, Va. 20110.

A. Culture of *Enterobacter* sp. 638

In one aspect, the invention relates to an isolated culture of *Enterobacter* sp. 638. *Enterobacter* sp. 638 is a non-phytopathogenic bacterial strain. The *Enterobacter* sp. 638 strain was isolated under aerobic conditions from surface-sterilized root and stem samples taken from hybrid poplar tree H11-11 that were grown in a silty loam soil with groundwater below it that was contaminated with carbon tetrachloride or trichloroethylene.

The *Enterobacter* sp. 638 strain includes a single circular chromosome of 4,518,712 bp with an overall G+C content of 52.98%, and it stably includes a plasmid pENT638-1 of 157,749 bp, having an overall G+C content of 50.57%. The pENT638-1 plasmid displays, based on GC content, at least four distinct regions. The pENT638-1 plasmid is related to F plasmids found in other *Enterobacteriaceae*. Plasmids of this family are involved in host interaction and virulence, such as pFra plasmid of the plague microbe *Yersinia pestis*. In pENT638-1, however, the pFra pathogenicity island is replaced by a unique 23-kb putative genomic island (flanked by an integrase gene and having a GC content that is significantly different than that of the rest of the plasmid).

An "isolated culture" refers to a culture of the microorganism that does not include other materials (i) which are normally found in soil in which the microorganism grows, and/or (ii) from which the microorganism is isolated. In addition, such a culture may be a culture that does not contain any other biological, microorganism, and/or bacterial species in quantities sufficient to interfere with the replication of the culture or to be detected by normal bacteriological, molecular biology, and/or chemical techniques.

B. Inoculant for a Plant

In another aspect, the invention relates to an inoculant for a plant. The inoculant includes an isolated culture of *Enterobacter* sp. 638 and a biologically acceptable medium. The terms "microbial inoculant" or "inoculant" refer to a preparation that includes an isolated culture of *Enterobacter* sp. 638.

To facilitate the culture of the *Enterobacter* sp. 638, the culture may be diluted, for example, with a suitable medium or carrier. A "biologically acceptable medium" refers to a medium that does not interfere with the effectiveness of the biological activity of *Enterobacter* sp. 638 and which is not toxic to *Enterobacter* sp. 638.

Examples of a biologically acceptable medium include a minimal salt medium with gluconate and a diluted rich medium (1/100 LB). The biologically acceptable medium may include carbon sources, such as the following exemplary compounds: D-mannitol, lactose, sucrose, arbutin, salicin, trehalose, D-mannose, L-arabinose, maltose, cellobiose, xylose, gluconate and glucose. Preferably, the medium includes glucose, sucrose, other plant derived sugars, and/or poplar extract to induce the induction of plant growth-promoting phytohormones (acetoin, 2,3-butanediol, see FIG. 5).

In one embodiment, the inoculant further includes a plant-growth promoting microorganism, including, for example, a plant-growth promoting endophytic bacterium, fungus, rhizosphere bacterium and/or a mycorrhizal fungus. Specific exemplary plant-growth promoting microorganisms include but are not limited to members of the genera *Actinobacter, Alcaligenes, Bacillus, Burkholderia, Buttiauxella, Enterobacter, Klebsiella, Kluyvera, Pseudomonas, Rahnella, Ralstonia, Rhizobium, Serratia,* and *Stenotrophomonas*.

C. Method for Increasing Growth

In another aspect, the invention relates to a method for increasing growth in a plant. The method includes applying an effective amount of a composition including an isolated culture of *Enterobacter* sp. 638 to the plant.

A "plant" as used herein refers to any type of plant, such as a tree, shrub, flower, herb, vine, or grass. The term "plant" also refers to any part of the plant, for example, to a whole plant, a plant part, a plant cell, or a group of plant cells, such as plant tissue, or progeny of same. Plantlets are also included within the meaning of "plant." Plants include, for example, any gymnosperms and angiosperms, both monocotyledons and dicotyledons, and trees.

Examples of monocotyledonous angiosperms include, but are not limited to, asparagus, field and sweet corn, barley, wheat, rice, sorghum, onion, pearl millet, rye and oats and other cereal grains, sugar cane, elephant grass, switch grass and miscanthus.

Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. In a preferred embodiment, the plant is a tomato. In another preferred embodiment, the plant is sunflower. In yet another preferred embodiment, the plant is tobacco.

Examples of woody species of plants include poplar, pine, sequoia, cedar, oak, etc. Tree species further include, for example, fir, pine, spruce, larch, cedar, hemlock, acacia, alder, aspen, beech, birch, sweet gum, sycamore, poplar, willow, and the like. In a preferred embodiment, the plant is a poplar.

As used herein, the term "increasing" growth refers to an increase in a growth characteristic of a plant treated with a method or composition of the invention, in which the increase in the growth characteristic is greater than the growth in a corresponding control plant when grown under identical conditions without application of the inventive method or composition. A "corresponding" control plant refers to a wild-type plant that is of the same type or species as the plant treated with a method or composition of the invention.

The increase in growth can be an increase in growth of a particular part of the plant, such as the roots, shoots, leaves, flowers, fruits, and/or seeds, or growth can be distributed throughout the entire plant. Means for measuring growth are known in the art.

Increased growth may include, for example, an increase in at least one, or a combination of, the following characteristics in the plant and/or a part of the plant: height, width, mass, an accumulation of radioactive carbon, an increase in dry weight, an increase in fresh weight and/or an increase in the rate of such increases over a specific period of time.

Increase in growth may also include, for example, an increase in the amount of fruit produced, a decrease in time to flowering, and/or an increase in the mass of vegetative parts that serve a useful purpose, such as roots or tubers from plants in which these parts are a food source.

The increase in growth may be an increase that is 2, 4, 5, 6, 8, 10, 20 (or more)-fold greater as compared to the growth of a corresponding control plant grown under identical conditions without application of the inventive method or composition. For example, a plant having increased growth as compared to the control plant may have 10%, 15%, 20%, 25%, 30%, 40%, 50%, 60% 70%, 75%, 80%, 90%, 100% or greater growth than the corresponding control plant grown under identical conditions without application of the inventive method or composition.

D. Method for Increasing Biomass

In a further aspect, the invention relates to a method for increasing biomass in a plant. The method includes applying an effective amount of a composition including an isolated culture of *Enterobacter* sp. 638 to the plant.

The term "biomass" refers to the dry weight or fresh weight of the plant. Biomass includes, for example, all plant parts unless otherwise stipulated, such as in reference to shoot biomass (all above ground plant parts), leaf biomass, and root biomass. The term "dry weight" refers to the weight of a plant that has been dried to remove the majority of cellular water. The term "fresh weight" refers to the weight of a plant that has not been dried to remove the majority of cellular water. Means for measuring biomass are known in the art.

The term "increasing biomass" refers to an increase in biomass of a plant treated with a method or composition of the invention, in which the increase in biomass is an amount greater than the amount of biomass in a corresponding control plant grown under identical conditions without application of the inventive method or composition.

The increase in biomass may be an increase that is 2, 4, 5, 6, 8, 10, 20 (or more) fold greater as compared to the biomass of a corresponding control plant grown under identical conditions without application of the inventive method or composition. For example, a plant having increased biomass as compared to the wild-type plant may have 10%, 15%, 20%, 25%, 30%, 40%, 50%, 60% 70%, 75%, 80%, 90%, 100% or greater biomass than the corresponding control plant grown under identical conditions without application of the inventive method or composition.

E. Method for Increasing Disease Tolerance and/or Resistance

In yet another aspect, the invention relates to a method for increasing disease tolerance and/or resistance in a plant. The method includes applying an effective amount of a composition including an isolated culture of *Enterobacter* sp. 638 to the plant. While not being limited to any particular theory, *Enterobacter* sp. 638 may increase disease tolerance and/or resistance in a plant due to a production of acetoin and 2,3-butanediol by *Enterobacter* sp. 638, or due to a production of the antimicrobial compounds 2-phenylethanol and 4-hydroxybenzoate, or via direct competition for essential nutrients via the synthesis of the siderophore enterobactin, and/or via the uptake of heterologously produced iron siderophore complexes by *Enterobacter* sp. 638.

The term "disease tolerance" refers to the ability of a plant to endure or resist a disease while maintaining the ability to function and produce despite the disease. A disease includes, for example, the presence of a pathology which adversely affects the viability of a plant, such as, for example, an infection by a pathogen (e.g., a fungus, virus, or bacteria) in and/or on the plant.

The term "disease resistance" refers to the ability of a plant to develop fewer disease symptoms following exposure to a disease than the corresponding control plant that does not exhibit disease resistance when grown under identical conditions and disease. Disease resistance includes complete resistance to the disease and/or varying degrees of resistance manifested as decreased symptoms, longer survival, or other disease parameters, such as higher yield, increased growth, increased biomass, accelerated fruit ripening, etc.

A disease may be, for example, a fungal infection such as Septoria, Melampsora, or septotina, a viral infection such as the poplar mosaic virus, and/or a bacterial infection, such as an infection from *Agrobacterium, Rickettsia,* or *Corynebacterium.*

The term "increasing" disease tolerance and/or resistance refers to an increase in disease tolerance and/or resistance of a diseased plant treated with a method or composition of the invention, in which the disease tolerance and/or resistance is greater than the disease tolerance and/or resistance in a corresponding control plant grown under identical conditions and disease.

The increase disease tolerance and/or resistance may be an increase that is 2, 4, 5, 6, 8, 10, 20 (or more) fold greater as compared to the tolerance and/or resistance of a corresponding control plant grown under identical conditions and disease exposure. For example, a plant having increased disease tolerance and/or resistance as compared to the wild-type plant may have 10%, 15%, 20%, 25%, 30%, 40%, 50%, 60% 70%, 75%, 80%, 90%, 100% or greater disease tolerance and/or resistance than the corresponding control plant grown under identical conditions without application of the inventive method or composition.

Methods for assessing disease tolerance and/or resistance are known in the art. For example, such methods may include observations and ratings of physical manifestations of disease symptoms, loss of plant vigor, or death, and activation of specific disease response genes, as compared to a control plant.

F. Method for Increasing Fruit and/or Seed Productivity

In yet a further aspect, the invention relates to a method for increasing fruit and/or seed productivity in a plant. The method includes applying an effective amount of a composition including an isolated culture of *Enterobacter* sp. 638 to the plant.

"Increasing productivity" refers to increasing the mass or number of fruit and/or seed produced by a plant treated with a method or composition of the invention, in which the increase in productivity is an amount greater than the amount of productivity in a corresponding control plant when grown under identical conditions without application of the inventive method or composition.

Methods of assessing an increase in productivity may include, for example, determining the number of fruits produced by the plant, the weight of individual fruits produced by the plant, the time to flowering in the plant, the time to fruit maturation in the plant, and/or the number of seeds produced by an individual fruit or flower of the plant.

Productivity is increased in a plant if, for example, the number of fruit produced by the plant is increased, the weight of individual fruits produced by the plant is increased, the time to flowering in the plant is decreased, the time to fruit maturation in the plant is decreased, and/or the number of seeds produced by an individual fruit or flower of the plant is increased when compared to a corresponding control plant when grown under identical conditions without application of the inventive method or composition.

The increase or decrease in productivity may be a respective increase or decrease that is 2, 4, 5, 6, 8, 10, 20 (or more) fold greater or less than the productivity of a corresponding control plant grown under identical conditions without application of the inventive method or composition. For example, a plant having increased productivity as compared to the control plant may have 10%, 15%, 20%, 25%, 30%, 40%, 50%, 60% 70%, 75%, 80%, 90%, 100% or greater productivity than the corresponding control plant grown under identical conditions without application of the inventive method or composition.

G. Method for Increasing Drought Tolerance and/or Resistance

In another aspect, the invention relates to a method for increasing drought tolerance and/or resistance in a plant. The method includes treating the plant with a composition that includes an isolated culture of *Enterobacter* sp. 638. While not being limited to any particular theory, *Enterobacter* sp. 638 may increase drought tolerance and/or resistance in a plant due to a production of acetoin and 2,3-butanediol by *Enterobacter* sp. 638.

The term "drought tolerance" refers to the ability of a plant to endure or resist drought conditions. "Drought" refers to a condition in which a plant is subjected to osmotic stress or reduced water potential. For example, drought may be caused by lack of available water for a period of time. Drought conditions may be assessed by comparing the amount of water required for growth or maturation a plant to the amount of water available to the plant. Drought conditions may be caused, for example, by lack of rainfall or irrigation, relative to the amount of water used internally or transpired by a plant.

The term "drought resistance" refers to the ability of a plant to develop fewer symptoms of water stress (e.g., lower productivity, leaf loss, death) than the corresponding control plant when grown under identical conditions of water stress. Drought resistance includes complete resistance to the effects of drought (no loss of productivity) or varying degrees of resistance manifested as decreased symptoms or longer survival.

Phenotypic assessment of symptoms may be used to determine whether, and to what extent, a plant is suffering from drought. For example, drought tolerance and/or resistance may be assessed by observing and rating wilting, growth arrest, death, productivity, leaf loss (e.g., leaf rolling, leaf distortion, leaf drop, leaf scorch), stem or twig dieback, photosynthetic efficiency, flowering, and yield level in a plant. In addition, drought tolerance and/or resistance of a plant may be assessed, for example, by biochemical or nucleic acid based assays to measure expression or activation of specific response genes in the plant.

Drought tolerance and/or resistance is increased in a plant if the plant demonstrates less severe symptoms of stress caused by the drought. For example, drought tolerance and/or resistance is increased if wilting, growth arrest, death, leaf loss (e.g., leaf rolling, leaf distortion, leaf drop, leaf scorch), and/or stem or twig dieback is decreased when compared to a corresponding control plant when grown under identical conditions without application of the inventive method or composition. Other examples of an increased drought tolerance and/or resistance include an increase in productivity, plant vigor, photosynthetic efficiency, flowering, and/or yield level in a plant when compared to a corresponding control plant when grown under identical conditions without application of the inventive method or composition.

Accordingly, the term "increasing" drought tolerance and/or resistance refers to an increase in drought tolerance and/or resistance of an impacted plant treated with a method or composition of the invention, in which the tolerance and/or resistance is greater than the drought tolerance and/or resistance in a corresponding control plant grown under identical conditions and water stress.

The increase drought tolerance and/or resistance may be an increase that is 2, 4, 5, 6, 8, 10, 20 (or more) fold greater as compared to the tolerance and/or resistance of a corresponding control plant grown under identical conditions and water stress. For example, a plant having increased drought tolerance and/or resistance as compared to the control plant may have 10%, 15%, 20%, 25%, 30%, 40%, 50%, 60% 70%, 75%, 80%, 90%, 100% or greater drought tolerance and/or resistance than the corresponding control plant grown under identical conditions without application of the inventive method or composition.

H. General Methods

Any method of applying a composition to a plant may be used in the methods of the present invention. Methods of applying a composition on and/or in a plant are known in the art. In one embodiment, the composition may be inoculated into the soil with the plant. In another embodiment, the inventive composition may be introduced to the plant roots through growth in a hydroponic medium or sprayed onto the leaves of a plant.

The composition of the invention may be applied to any part of the plant, including the seeds through the use of a suitable coating mechanism or binder. The inventive composition may either be applied on the plants prior to planting or be introduced into the plant furrows during planting. As another example, the inventive composition may be applied to the roots of the plant. The inventive composition may be prepared with or without a carrier and sold as a separate inoculant to be inserted directly into the furrows into which the plant is planted.

In accordance with the methods of the invention, an effective amount of the inventive composition is that amount sufficient to establish sufficient bacterial growth such that the desired result is achieved in the treated plant. An effective amount of the inventive composition may be determined by known means in the art for a particular plant species. For example, inoculation with the inventive composition may be conducted in hydroponics for six days, and the bacterial suspension may be refreshed after three days following inoculation.

In one embodiment, the effective amount may, for example, be any amount from about $10^1$ to about $10^{12}$ cells per plant. In another embodiment, the effective amount is a cell concentration from about $10^5$ to about $10^{10}$ CFU/ml of inoculum, more preferably from about $10^6$ to $10^8$ CFU/ml, and most preferably about $10^8$ CFU/ml. In yet another embodiment, the inventive composition can be mixed with the soil in an amount of from about $10^5$ to $10^{10}$ cells per gram of soil.

EXAMPLES

Example 1

Isolation and Characterization of *Enterobacter* sp. 638

Root and shoot samples were collected from the 10-year-old hybrid poplar tree H11-11 (*Populus trichocarpa_P. deltoides*) that had been growing in the presence of carbon tetrachloride (12 ppm homogeneously) for 8 years at an experimental site in Washington State. In addition, native willow (*Salix gooddingii*) material was collected from 5-year-old native plants that had been growing in the presence of both trichloroethylene (18 ppm) and carbon tetrachloride (12 ppm) for 5 years. Cuttings were removed from the plants with clippers that were washed with ethanol between cuts and placed in acetone-rinsed volatile organic analysis vials which were placed on ice for shipment from the field. Roots and shoots were treated separately. Fresh root and shoot samples were vigorously washed in distilled water for 5 min, surface sterilized for 5 min in a solution containing 1% (wt/vol) active chloride (added as a sodium hypochlorite [NaOCl] solution) supplemented with 1 droplet Tween 80 per 100 ml solution, and rinsed three times in sterile distilled water. A 100-μl sample of the water from the third rinse was plated on 869 medium (25) to verify the efficiency of sterilization. After sterilization, the roots and shoots were macerated in 10 ml of 10 mM MgSO4 using a Polytron PT1200 mixer (Kinematica A6). Serial dilutions were made, and 100-μl samples were plated on nonselective media in order to test for the presence of the endophytes and their characteristics.

*Enterobacter* sp. 638 was isolated under aerobic conditions from surface-sterilized root and stem samples taken from hybrid poplar tree H11-11 and native willow (*Salix gooddingii*) that were grown in a silty loam soil with groundwater below it that was contaminated with carbon tetrachloride or trichloroethylene and carbon tetrachloride, respectively. Its total genomic DNA was extracted and used to amplify the 16 rRNA gene. 16S rRNA genes were PCR amplified using the standard 26F-1392R primer set (Amann, 1995)

Example 2

Screening of Endophytic Bacteria for Plant Growth-Promoting Properties in Poplar Inocula (250-ml culture) were prepared by growing endophytic bacteria in ⅒-strength 869 medium (25) at 30° C. on a rotary shaker until a cell concentration of $10^9$ CFU/ml was reached (optical density at 660 nm [OD660] of 1). The cells were collected by centrifugation, washed twice in 10 mM MgSO4, and suspended in ⅒ of the original volume (in 10 mM MgSO4) to obtain an inoculum with a cell concentration of $10^{10}$ CFU/ml. Per microbial strain tested, seven cuttings from poplar (*Populus deltoides* x *P. nigra*) DN-34 of approximately 30 cm were weighed and placed in a 1-liter beaker containing 0.5 liter of a half-strength sterile Hoagland's nutrient solution (5), which was refreshed every 3 days. The cuttings were allowed to root for approximately 4 weeks until root formation started. Subsequently, a bacterial inoculum was added to each jar at a final concentration of $10^8$ CFU/ml in half-strength Hoagland's solution. After 3 days of incubation, cuttings were weighed and planted in nonsterile sandy soil and placed in the greenhouse with a constant temperature of 22° C. and 14 h light-10 h dark cycle with photosynthetic active radiation of 165 mmol/m2s. After 10 weeks, plants were harvested, and their total biomass, their increase in biomass, and the biomass of different plant tissues were determined. Data were also collected from non-inoculated control plants. Growth indexes were calculated as (Mt−M0)/M0 after 10 weeks of growth in the presence or absence of endophytic inoculum, where M0 is the plant's weight (g) at week 0 and Mt is the plant's weight (g) after 10 weeks. The statistical significance of the results was confirmed at the 5% level using the Dunnett test. To determine the effects of endophytic bacteria on the rooting of poplar DN-34, cuttings were treated as described above, except that the endophytic inoculum was added from day 1.

*Enterobacter* sp. 638 isolated from poplar was tested for its capacity to improve the growth of their host plants, along with other endophytic gammaproteobacteria found in poplar trees. *Burkholderia cepacia* Bu72, an endophyte originally isolated from yellow lupine which was found to have plant growth-promoting effects on poplar trees, and *Cupriavidus metallidurans* CH34 (also referred to as *Ralstonia metallidurans* CH34), a typical soil bacterium with no known plant growth promoting effects, were included as positive and negative controls, respectively. Also, non-inoculated cuttings were used as controls.

After root formation in hydroponic conditions and subsequent endophytic inoculation, the poplar DN-34 cuttings were planted in a marginal sandy soil and allowed to grow for 10 weeks, after which the plants were harvested and their biomasses were determined.

After 10 weeks of growth, poplar trees inoculated with *M. populi* BJ001 had less new biomass than the controls (FIG. 1) (P<0.05). Poplar cuttings inoculated with *Enterobacter* sp. 638 (P=0.018) and *B cepacia* BU72 (P=0.042) showed statistically better growth than the control plants (FIG. 1), as was reflected by their growth indexes. The plant growth-promoting effects of *Enterobacter* sp. 638 and *B. cepacia* BU72 were reproducible in independently performed experiments.

Under the greenhouse conditions tested, no differences in growth indexes were found between those of the non-inoculated control plants and those for plants inoculated with *S. maltophilia* R551-3, *P. putida* W619, and *S. proteamaculans* 568; their growth was comparable to that observed for plants inoculated with *C. metallidurans* CH34. Also, control plants and plants inoculated with the endophytic bacteria appeared healthy, except for plants inoculated with *M. populi* BJ001, which showed signs of stress, including chlorosis of the leaves.

Example 3

Screening of Endophytic Bacteria for Plant Growth-Promoting Properties in Tobacco Because *Nicotiana* species are used in the laboratory as large-plant models for transformation and metabolite studies, it would be useful to be able to use such a plant for study, even if it is not useful for field applications. *Nicotiana xanthi* seedlings were started in soilless growing medium, and after development of primary leaves, were transferred to hydroponic solutions. After one week, plants were placed in solutions containing $10^8$ CFU *Enterobacter* sp. 638. After 3 days, inoculums were refreshed, and after an additional three days, plants were placed in pots in the greenhouse.

Plant growth was monitored weekly, and time to onset of flowering was recorded. Plants reached full size more rapidly than non-inoculated plants, and the majority of plants were in flower one month before the same number of non-inoculated plants were in flower.

Example 4

Effects of Endophytic Bacteria on Poplar Root Development

To further test the effects of endophytic bacteria on root development, rooting experiments were performed in the presence and absence of gfp-labeled derivatives of *Enterobacter* sp. 638. Root formation was very slow for non-inoculated plants. In contrast, for cuttings that were allowed to root in the presence of the selected endophytes, root formation was initiated within 1 week, and shoot formation was more pronounced compared to that of the non-inoculated plants (FIG. 2A). After 10 weeks, root formation for the non-inoculated controls was still poor; however, for plants inoculated with *Enterobacter* sp. 638, roots and shoots were well developed (FIG. 2B). Fluorescence microscopy was used to visualize the internal colonization of the plant roots by the gfp-labeled strains, confirming their endophytic behavior. The formation of microcolonies on the root surface, as observed for *P. putida* W619, were absent on plants inoculated with *Enterobacter* sp. 638, where only internal colonization was observed. No gfp expression was detected for roots from non-inoculated control plants.

Example 5

Effect of Endophytic Bacteria on Fruiting and Flowering Productivity

To test the effect of the endophytic bacteria of mass of fruit production, tomato seeds (heirloom variety Brandywine, Park Seed) were started in a perlite/water matrix, and then transferred to a hydroponic solution of ½ strength Hoagland's solution. When plants were approximately 3 inches tall, they were transferred to solutions containing $10^8$ CFUs per mL of endophytic bacteria as described above. Three days after inoculation, seedlings were planted in the greenhouse in ProMix, a commercial potting mix. Dates of first fruit set and total mass of tomatoes were recorded for three months. Tomato plants inoculated with *Enterobacter* 638 had a 10% increase in fruit productivity over non-inoculated plants. Non-inoculated plants produced 82 fruits with a total mass of 22.374kg, while the inoculated plants produced 90 fruits with a combined mass of 24.909 kg (FIG. 3).

Sunflower seedlings (Mammoth, Park Seed) were started using the method described, and time to flowering was recorded. Under greenhouse conditions, inoculated sunflowers started flowering 5 days earlier than non-inoculated plants, and 50% were in flower while only 10% of the non-inoculated plants were flowering; 100% of the inoculated plants were flowering while only 70% of the non-inoculated plants were flowering (FIG. 4).

Example 6

Drought Resistance

Hybrid poplar hardwood cuttings (OP-367 *Populus deltoides* x *P. nigra*) were placed in water for three days to initiate root formation, and were then moved to a ½ strength Hoagland's solution containing $10^8$ CFU per mL of endophytic bacteria for three days. Cuttings were then planted in pots containing garden soil and grown in the greenhouse for three months with surplus water supplied. After three months, watering of the plants was suspended, and time to senescence was monitored. Inoculated plants on average showed a 20% delay in the onset of drought symptoms, as compared to non-inoculated plants.

Example 7

Disease Resistance

Due to the increased vigor of the plants, as well as genetic elements present in the endophytic bacteria, that inoculated plants will prove to be more resistant to pathogen colonization and that symptoms will be less evident on inoculated plants.

Hybrid poplar cuttings, both H11-11 (highly susceptible to fungal disease) and OP-367 (resistant to fungal disease) will both be inoculated as described. Plants will planted in sterile potting mix, and grown until six to eight leaves are present. Plants will then be exposed to fungal pathogens, and monitored for both time of onset and severity of physical symptoms of infection. Plants can also be analyzed to determine activity of known disease responsive genes.

Example 8

Genome Structure and General Features

The genome of the gamma-proteobacterium *Enterobacter* sp. 638 includes a single circular chromosome of 4,518,712 bp with an overall G+C content of 52.98%, and it includes a plasmid pENT638-1 of 157,749 bp, having an overall G+C content of 50.57% (Table 1). The chromosome of *Enterobacter* sp. 638 displays a GC skew transition, which corresponds with its replication origin (oriC) and terminus. The oriC site contains a perfect DnaA-binding box (TTATC-CACA), which is located 31,985 bp upstream of the dnaA ATG start codon (at coordinate 4,487,245 bp).

The pENT638-1 plasmid displays, based on GC content, at least four distinct regions. The plasmid is includes an ancestral backbone, which is common to F-family plasmids and contains the plasmid's basic functions for transfer and replication, and of regions that were likely acquired via horizontal gene transfer. These regions in the pENT638-1 plasmid display a codon usage matrix different from the rest of the species of *Enterobacteriaceae*. In addition, these regions have no synteny to sequenced chromosomes or plasmids from closely related strains, and these regions interestingly encode genes related to plant adhesion and colonization. The stable maintenance in *Enterobacter* sp. 638 of pENT638-1 and these regions, which presumably play a role in the successful interaction between *Enterobacter* sp. 638 and its plant host, seems important regarding the presence of six relBE toxin/anti-toxin (TA) systems.

In contrast, the chromosome of *Enterobacter* sp. 638 encodes only three couples of toxin/anti-toxin (Ent638_0434-0435, Ent638_0476-0477, and Ent638_2066-2067). This low number is representative for host-associated organisms.

The chromosome encodes 4395 putative coding sequences (CDS) representing a coding density of 87.9%, and plasmid pENT638-1 encodes 153 putative CDS having a coding density of 80.4%. After their manual annotation, 3562 CDS (78.3%) could be assigned to a putative biological function, while 835 CDS (18.4%) were annotated as hypothetical proteins of unknown function. Conserved hypothetical proteins are represented by 684 CDS (15.0%), while 151 CDS (3.3%) had no homology to any previously reported sequence. Using the COGnitor module from the MaGe system, 3597 CDS (79.1%) could be assigned to one or more COG functional classes (see FIG. 9). The repartition of *Enterobacter* sp. 638 CDS among the different COG classes is very similar to what is observed for *E. coli* K12. The three most abundant classes are amino acid (E), carbohydrate (G) and inorganic iron (P) transport and metabolism and represent more that 37% of all CDS, pointing to the symbiotic life styles of *Enterobacter* sp. 638 and *E. coli* K12 that require efficient uptake of host-provided nutrients. Seven sets of 5S, 16S, 23S rRNA genes and one additional 5S rRNA gene were found. A total of 83 tRNA genes with specificities for all 20 amino acids, and a single tRNA for selenocysteine were identified.

The genome of *Enterobacter* sp. 638 encodes 8 Sigma factors:fliA (Ent638_2509; Sigma 28), three rpoE-like Sigma 24 (Ent638_3060, Ent638_3117 and Ent638_3389), rpoS (Ent638_3212, Sigma 38), rpoD (Ent638_3473, Sigma 70), rpoN (Ent638_3638, Sigma 54) and rpoH (Ent638_3865, Sigma 32).

*Enterobacter* sp. 638 encodes an active dam methylase involved in the adenine methylation at GATC sites, as was confirmed by MboI and Sau3AI digestion of the DNA, the first enzyme being unable to digest the methylated *Enterobacter* sp. 638 DNA.

On the genome of *Enterobacter* sp. 638 one hundred palindromic repeats were found unevenly distributed over the chromosome. These hairpin loop forming repeats (with XX(X) mainly being TGT/ACA or AC/TG) are often located in duplicate or triplicate at the 3' end of genes and presumably play a role in transcription termination.

Eight Insertion Sequence (IS) elements were found on the genome of *Enterobacter* sp. 638: two from the IS3/IS51 family (one composed of three ORFs with a frameshift (Ent638_0739, Ent638_0740, Ent638_0741) and one composed of a single ORF (Ent638_0060)), one IS element from the IS110 family (Ent638_1530), and three IS elements from the IS481 family (Ent638_2980, Ent638_3160 and Ent638_3288). Some of these IS elements are delimitating putative genomic islands (see section below).

Plasmid pENT638-1 possesses two complete IS elements, one from the Tn3 family composed of one ORF (Ent638_4224) and one from the IS3/IS407 family composed of two ORFs (Ent638_4320 and Ent638_4321), as well as two truncated transposases from the latter family. The complete IS and the truncated transposase from the IS3/IS407 families are flanking a large region encoding genes involved in plasmid maintenance and replication (sopAB, repA) and genes involved in plasmid transfer by conjugation (tra). This 75 kb region can be considered as the pENT638-1 backbone.

When comparing the genome of *Enterobacter* sp. 638 with those of closely related strains, *Enterobacter cancerogenus* ATCC 35316 was determined to be the closest genome with 80.4% of the CDS in synteny with *Enterobacter* sp. 638, then *Klebsiella pneumoniae* 342 and MGH 78578 (both with 74% of the CDS in synteny), followed by *Citrobacter koseri* ATCC BAA-895 (73%) and then the *Escherichia coli* species (between 63 to 73%)

The specific adaptation of *Enterobacter* sp. 638 to its plant host was scrutinized through genome comparison with other plant associated microbes and the gastrointestinal bacterium *E. coli* K12 (MG1655). This strain, chosen as a reference organism because it is the best annotated bacterial genome, shared (criteria 80% of identity on 80% of the protein length) 2938 syntenic CDS (69.2% of their genome) with *Enterobacter* sp. 638. The syntenic regions are grouped in 304 syntons with an average number of 10.5 CDS per synton.

Fifty-six regions were identified on the *Enterobacter* sp. 638 genome, which were not in synteny with the genomes of closely related bacteria. Among them, eighteen regions met the criteria for putative genomic islands (highlight in grey in table 2). These genomic islands carry genes encoding proteins involved in sugar transport (PTS system), adhesion, pectate utilization, iron uptake trough siderophore receptors, nitrate reduction, pilus biosynthesis, as well as many others transporters and regulators. Region number 47 is an illustrative example of the acquisition of a genomic island containing genes involved in adaptation for an endophytic lifestyle. This region encodes a putative pectate transporter and degradation proteins, which may allow strain 638 to grow on pectate (an important plant synthesized compound) as a carbon source. This genomic island is flanked by an integrase gene and inserted into a tRNA-Gly site.

Eight phages and one putative integrated plasmid were found on the chromosome. A total of 302 phage proteins, including 18 putative integrase genes, were identified.

In addition, the *Enterobacter* sp. 638 chromosome contains a region with Clustered Regularly Interspaced Short Palindromic Repeats (CRISPR) located next to six genes (Ent638 1401-1406) encoding CRISPR-associated sequences (Cas). CRISPR are likely to provide acquired tolerance against bacteriophages. Six of the eight prophages arc flanking by regions, which lack synteny with the corresponding regions in closely related bacteria such as *E. coli* K12, O157-H7 and UTI89, *Klebsiella pneumoniae* MGH 78578 or *Citrobacter koseri* BAA-895, and that may have been acquired through phage transduction. These regions contain genes important in bacteria/plant interactions such as amino-acid and iron/siderophore transporters, haemolysin (HCP), and a hemagglutinin protein and transporter (Table 2). Until now, the inter- or extra-cellular mobility of the genomic islands, phages and IS elements was not experimentally demonstrated.

Example 9

Survival in the Plant Rhizosphere: Overview of *Enterobacter* sp. 638 Metabolic Capabilities In general, poplar is multiplied by cuttings, and since the number of endophytes in cuttings is very low, many species of endophytic bacteria have to survive in the soil prior to colonizing poplar. *Enterobacter* sp. 638 is well adapted to survive in the plant rhizosphere because it encodes many transporters involved in carbohydrate, amino-acids and iron uptake, as well as some heavy metal resistance genes. Most of the metabolic pathways described below were confirmed by cultivating strain 638 under selective growth conditions (Taghavi et al. 2009).

Carbohydrate metabolism

The *Enterobacter* sp. 638 genome encodes all the pathways for central metabolism, including the tricarboxylic acid cycle, the Entner-Doudoroff, the EmbdenMeyerhof-Parnas and the pentose-phosphate pathways. The strain is unable to grow autotrophically, but can use a large variety of compounds as carbon sources: D-mannitol, lactose, sucrose, arbutin, salicin, trehalose, D-mannose, L-arabinose, maltose, cellobiose, xylose, gluconate and glucose (Taghavi et al. 2009). *Enterobacter* sp. 638 possesses a lactase (lacZ, Ent638_0928), a xylose isomerase (Ent638_0156) and a xylulokinase (Ent638_0157). Lactose utilization as a sole carbon source is a characteristic of the *Enterobacter*iaceae. *Enterobacter* sp. 638 has the genetic capability to grow on malonate, it genome contains a cluster of nine genes (mdcABCDEFGHR, Ent638_3779-Ent638_3772) involved in malonate decarboxylation that catalyze the conversion of malonate into acetate.

The diversity of sugar utilization might be related to the diversity of glycoside hydrolases. The *Enterobacter* sp. 638 genome carries 55 genes coding putative glycoside hydrolases, representing 24 different families (CAZy database). In contrast, it should also be mentioned that the human pathogen *Enterobacter sakazakii* possesses 63 glycoside hydrolases (CAZy database).

Plant pathogenic bacteria and fungi gain access by actively degrading plant cell wall compounds using glycoside hydrolases including cellulases/endoglucanases (including members of the glycoside hydrolase families GH5, GH9, GH44, GH48 and GH74), lichenases (GH16) and xylanases (GH10, GH11). No glycoside hydrolases representing putative members of endo-, exo-, cellulase and hemicellulase families commonly used to break down plant cell wall polymers were encoded on the *Enterobacter* sp. 638 genome. This observation is consistent with the non phytopathogenic behaviour of *Enterobacter* sp. 638. However, it should be noted that two endo-1,4-D-gluconases (GH8) (bcsZ: Ent638_3928, Ent638_3936) were found as part of a bacterial cellulose synthesis locus.

Uptake of Plant Nutrients

Organisms living in symbiotic association, like *Enterobacter* sp. 638 and its poplar host, for example, need to share resources, therefore, it is expected that the genome of *Enterobacter* sp. 638 encodes a large diversity of transporters that will allow it to take up plant-released nutrients. A total of 631 ORFs encode for putative transporter proteins: among them 295 encoded ABC transporters (including one phosphate transporter), 81 encoded transporters from the major facilitator superfamily (MFS), 41 encoded transporters from the phosphotransferase system family (PTS) and 14 encoded transporters from the resistance nodulation and cell division family (RND) (see complete list of putative transporters and their substrates in SOM). This observation is consistent with the plant associated life style of *Enterobacter* sp. 638, which requires efficient uptake of plant synthesized nutrients, including those released into the rhizosphere.

The *Enterobacter* sp. 638 genome encodes many PTS transporters. Phylogenetic analysis was used to assign substrate specificity to the *Enterobacter* sp. 638 PTS transporters: 7 belonged to the α-glucosides (for uptake of glucose, N-acetylglucosamine, maltose, glucosamine and α-glucosides), 7 to the β-glucosides (for uptake of sucrose, trehalose, N-acetylmuramic acid and β-glucosides), 2 were fructose PTS transporters (for uptake of fructose, mannitol, mannose and 2-O-α-mannosyl D-glycerate) and 6 were lactose PTS transporters (for uptake of lactose, cellobiose and aromatic β-glucosides).

Resistance to Heavy Metals

The *Enterobacter* sp. 638 genome carries genes putatively involved in copper resistance, including a P-type ATPase CopA (Ent638_0962) whose expression is regulated by CueR (Ent638_09630), the copper efflux operon cusABCF (Ent638_1157-1154), the multiple copper oxidase CueO (Ent638_0671), and an operon coding for the putative CopC and CopD copper resistance proteins (Ent638_2411-12). Interestingly, the strain failed to grow on 284 glucose minimal medium in the presence of 100 μM $Cu(NO_3)_2$.

The *Enterobacter* sp. 638 genome also encodes an arsenic/arsenate resistance cluster that was found next to the origin of replication of plasmid pENT638-1 (arsHRBC, Ent638_4254-Ent638_4257), and strain 638 was found to grow successfully on 284 glucose minimal medium in the presence of 200 μM arsenate (as $Na_2HAsO_4$).

The presence of arsenate and putative copper resistance genes is not unexpected, as *Enterobacter* sp. 638 was isolated from poplar growing in the area which was impacted by emissions from the ASARCO smelter in Tacoma, Wash., a copper smelter that during operations from 1905 through 1982 was considered to be one of the largest arsenic emission sources in the USA.

Other heavy metal resistance genes located on the chromosome include a putative chromate reductase (YieF or ChrR, Ent638_4144) and a P-type efflux ATPase ZntA (Ent638_3873) involved in zinc/cadmium/cobalt resistance. Strain 638 was able to grow on 284 glucose minimal medium in the presence of 500 μM $ZnSO_4$, 500 μM $CdCl_2$, 100 μM $CoCl_2$, and 50 μM $NiCl_2$. Although it could be argued that these genes are also present in other *E. coli* species, their presence may be enough to provide a selective advantage over other bacteria to survive in the rhizosphere, especially when these metals are present.

Heavy metals are also important cofactors, and the *Enterobacter* sp. 638 genome encodes several genes involved in heavy metal uptake and efflux. Genes were found for ABC transporters involved in zinc (znuACB, Ent638_2426-2428) and nickel (nikABCDE, Ent638_1834-Ent638_1838) uptake. Nickel is an essential cofactor for urease (Dosanjh et al. 2007), and unlike *E. coli* K12 and *S. proteamaculans* 568, *Enterobacter* sp. 638 is able to convert urea into ammonia (ureABC, Ent638_3464-Ent638_3466).

Oxidative Stress, Counteracting the Plant's Defense Mechanism

Plants use a variety of defense mechanisms against bacterial, viral and fungal infections, including the production of reactive oxygen species (ROS) (superoxide, hydroperoxyl radical, hydrogen peroxide and hydroxyl radical species), nitric oxide and phytoalexins. Prior to root colonization, strain 638 has to survive in an oxidative rhizosphere environment. The *Enterobacter* sp. 638 chromosome encodes three superoxide dismutases: SodA, a Mn superoxide dismutase (Ent638_4063); SodB a Fe superoxide dismutase (Ent638_1191); and SodC, a Cu/Zn superoxide dismutase (Ent638_1801). It also contains three catalases, KatE (Ent638_1712), KatN (Ent638_3129) and KatG (Ent638_4032), three hydroperoxide reductases, ahpC (Ent638_0872 and Ent638_1145) and ahpF (Ent638_1146), two additional hydroperoxide reductases (a putative ahpC Ent638_3391 and Ent638_0498 having an AhpD domain), a chloroperoxidase (Ent638_1149), and two thiol peroxidases (Ent638_2151 and Ent638_2976).

We also identified a putative organic peroxide resistance protein (ohr, Ent638_0518) located next to its organic peroxide sensor/regulator (ohrR, Ent638_0519).

*Enterobacter* sp. 638 seems able to detoxify free radical nitric oxide by the presence of a flavohemoprotein nitric oxide dioxygenase (Ent638_3037) and an anaerobic nitrate reduction operon (nor RVW, Ent638_3181-3183). The expression of the oxidative stress response systems is controlled via complex regulatory networks. A key regulator is the hydrogen-peroxide sensor OxyR (Ent638_4025), which activates the expression of a regulon of hydrogen peroxide-inducible genes such as katG, gor (glutathione reductase, Ent638_3913), ahpC, ahpF, oxyS (a regulatory RNA, Ent638_misc_RNA_29), dpsA (a DNA protection during starvation protein, Ent638_1299), fur (a DNA-binding transcriptional dual regulator of siderophore biosynthesis and transport, Ent638_1198) and grxA (glutaredoxin, Ent638_1364), all of which are present in *Enterobacter* sp. 638. Three glutathione S-transferase (GST) genes (Ent638_0139, Ent638_0268 and Ent638_1329), a glutathione ABC transporter (GsiABCD, Ent638_1323-1326), two glutathione peroxidase (Ent638_1732 and Ent638_2699), a gamma-glutamate-cysteine ligase (GshA, Ent638_3168), glutathione synthetase (GshB, Ent638_3351) and gamma-glutamyltranspeptidase (GGT, Ent638_3850) were found on the genome of *Enterobacter* sp. 638. An AcrAB (Ent638_0943-0944) locus, belonging to RND family of transporters was also identified on the *Enterobacter* sp. 638 genome.

Example 10

Endophytic Colonization and Establishment in the Host Plant

Endophytic colonization of a plant host can be divided into four step process (van der Lelie et al. 2009).
Step 1: Moving Toward the Poplar Roots: Motility/Chemiotaxis

*Enterobacter* sp. 638 is well equipped to actively move towards plant roots, the preferred site of endophytic colonization. Its genome contains three flagellar biosynthesis operons (flgNMABCDEFGHIJKL, flhEAB fimA yralJ lpfD cheZYBR tap tar csuEDCAB int cheWA motBA flhCD fliYZA fliCDSTEFGHJKLMNOPQR, Ent638_2445-2541 and fliEFHIJKLMNOPQR).

However, the flh operon of *Enterobacter* sp. 638 contains two insertions of pili biosynthesis genes. One of these regions (csu) is flanked by an integrase, pointing to later acquisition. *Enterobacter* sp. 638 also has a large number of pilus/fimbriae biosynthesis genes (at least 60 genes). In *Enterobacter* sp. 638, the pilus/fimbriae biosynthesis genes are grouped in 10 distinct regions. Determinants involved in chemiotaxis (che) were also discovered inside the flagellar biosynthesis gene cluster.
Step 2 and 3: Adhesion and Colonization of the Roots Surface In *Enterobacter* sp. 638, several genes were identified encoding proteins involved in the putative adhesion to the root. Many are located on genomic islands or on plasmid pENT638-1, pointing towards a specific role of this plasmid during this step of the plant root colonization. In particular, pENT638-1 contains a 23 kb putative genomic island (flanked by an integrase gene, and having a GC % of 56.2, which is significantly higher that the rest of the plasmid), as well as a putative srfABC operon. The exact function of the srfABC operon remains unclear, but it is believed to be involved in host colonization.

Many other genes involved in plant invasion are present on pENT638-1, and include putative proteins with an autrotransporter domain (secretion type V) and a virulence/adhesion domain (hemagglutinin (Ent638_4267), pertactin (Ent638 4201 and Ent638 4206) and adhesion (Ent638 4317)).

Hemagglutinin: The chromosome of *Enterobacter* sp. 638 encodes two putative hemagglutinin proteins (Ent638_0148, Ent638_3119), and a cluster composed of five genes encoding for filamentous hemagglutinin (Ent638_0052-0057).

In addition, several genes were found on the chromosome of *Enterobacter* sp. 638 encoding for autotransporter proteins with a pectin lyase/pertactin domain (Ent638_1775, Ent638_0318, Ent638_0501), or an adhesion domain (Ent638_1867, Ent638_3408).

The two *Enterobacter* sp. 638 yadA genes (Ent638_1867 and Ent638_4317) both encode a protein with an autotransporter domain and an invasin/adhesion domain. The YadA protein might promote plant colonization/invasion, but could also represent a remnant of an ancient enteric lifestyle.

The hemagglutinin gene on pENT638-1 (Ent638_4267) is surrounded by two RelB/E toxin/anti-toxin systems. It is hypothesized that the Ent638_4267 hemagglutinin must play an important role in root adhesion for been stabilized in this way on the pENT638-1. Together with the hemagglutinin gene Ent638_4267, two genes (Ent638_4265-4266) coding for a protein containing a tetratricopeptide (TPR-2) repeat domain were identified, putatively involved in protein-protein interaction and the correct assembly of the adhesion apparatus.

Type I and IV pili: Six putative usher proteins were found on the *Enterobacter* sp. 638 genome (Ent638_0084, Ent638_0403, Ent638_0990, Ent638_1071, Ent638_2450, and Ent638_2459). This number is much higher than the average number of usher proteins found in other genera of plant associated bacteria.

On the chromosome of *Enterobacter* sp. 638, 56 genes involved in pili/curli/fimbriae biosynthesis were identified, including 6 clusters of type-I pili biosynthesis genes (Ent638_0074-0086, Ent638_0401-0409, Ent638_0987-0994, Ent638_1068-1072, Ent638_2448-2451, Ent638_2458-2462). The last two clusters are flanked and separated by genes involved in chemiotaxis and motility (flagellar biosynthesis) (see section motility), and are possibly involved in biofilm formation on abiotic surfaces. This region (Ent638_2445-2541) represents a nice example of clustering genes involved in different aspects of plant roots colonization (chemiotaxis, motility, and adhesion).

Type IV pili. On the *Enterobacter* sp. 638 genome, two clusters of type-IV pili biosynthesis genes were identified, (Ent638_0650-0652, and Ent638_3266-3268), as well as a cluster of putative uncharacterized pilus biosynthesis genes (Ent638_3804 and Ent638_3808) that are possibly involved in DNA uptake.

Curli fibers. Structurally and biochemically, curli belongs to a growing class of fibers known as amyloids. On the genome of *Enterobacter* sp. 638, one cluster for curli biosynthesis (Ent638_1553-1559) was identified.
Cellulose Biosynthesis Consistent with its non pathogenic behavior the genome of *Enterobacter* sp. 638 does not encode proteins involved in cellulose degradation. However, an operon responsible for cellulose biosynthesis was identified (Ent638_3927-3940).
Virulence Microsopic studies showed that *Enterobacter* sp. 638 colonizes the root xyleme between the lumen of the lenticels; no intracellular colonization was observed (Taghavi et al. 2009).

Although *Enterobacter* sp. 638 was never found to act as an opportunistic pathogen in plant colonization studies, its genome codes for several proteins putatively involved in virulence. It should be noted that virulence may also require close interaction between the bacterium and its host, similar to what may be required for endophytic colonization. One gene (ygfA, Ent638_3317) coding for an inner membrane hemolysin (family III), a partial CDS (Ent638_0251) containing a putative hemolysin domain, and three genes hcp coding for virulence factors (Ent638_0829, Ent638_2912 and Ent638_3004) were identified.

Other putative virulence factors include pagC (Ent638_3136) and msgA (Ent638_1656), which are required for virulence and survival within macrophages, and putative virK genes (Ent638_1394 and Ent638_2409), whose product is required for the expression and correct membrane localization of VirG (Ent638_3560) on the bacterial cell surface.

However, no genes encoding for a type III secretion system, which is a prerequisite for an active virulent life style typical for pathogens such as *Erwinia* and *P. syringae*, were identified on the *Enterobacter* sp. 638 genome.

Finally, similar to the pENT638-1 plasmid, a srfABC operon (Ent638_2108-Ent638_2110) was found on the *Enterobacter* sp. 638 chromosomes. The function of these genes in endophytic behavior remains unclear.

Step 4: Invasion of the Root and in Planta Establishment Via Active Colonization

*Enterbacter* sp. 638 may enter the plant roots at sites of tissues damage because its genome sequence does not encode endo/exo-cellulases or hemicellulases that would allow endophytic colonization via the active breakdown of plant cell walls.

Pectin/Pectate Degradation

Although *Enterobacter* sp. 638 is not able to grow on pectin (poly(1,4-alpha-D-galacturonate)) as a sole carbon source, its genome contains a genomic island encoding the genes involved in the degradation of pectate, the demethylated backbone of pectin and a constituent of the plant cell wall. The ability of *Enterobacter* sp. 638 to degrade pectate could play a role in colonizing the interspatial region between plant cells.

A secreted pectate lyase, PelB, involved in the cleavage of pectate into oligosaccharides with 4-deoxy-alpha-D-galact-4-enuronosyl groups at their non-reducing ends was found next to an oligogalacturonate-specific porin, KdgM, involved in the uptake of oligogalacturonides into the periplasm. A periplasmic pectinase, PelX, encoded by a different region of the genome, is involved in periplasmic degradation of oligogalacturonide.

On another region, a carbohydrate uptake ABC transporter, TogMNAB, involved in the translocation of oligalacturonide across the inner membrane and several additional proteins, Ogl, KduI and KduD, involved in the degradation of oligogalacturonide into 2-dehydro-3-deoxy-D-gluconate, were identified. KdgK and KdgA, involved in D-glucuronate metabolism, further degrade 2-dehydro-3-deoxy-D-gluconate into pyruvate and 3-phosphoglyceraldehyde, both compounds of the general cellular metabolism. This region, which is flanked by a transposase from the IS481 family, might have been acquired via horizontal gene transfer. The proteins UxaA, UxaB, and UxaC, necessary for the alternative pathway to degrade galacturonate into 2-dehydro-3-deoxy-D-gluconate, are also encoded by the *Enterobacter* sp. 638 chromosome. The degradation of pectate has to be well regulated in order to avoid a pathogenic effect.

Plasmid pENT638-1 carries two neighboring genes (Ent638_4201, Ent638_4206) encoding for autrotransporter proteins with a pectin lyase domain. These proteins may be involved in the adhesion of *Enterobacter* sp. 638 to the poplar roots or as part of a colonization mechanism that involves the export of enzymes able to lyse the cell walls of root cells. Between these two genes, two component transcriptional regulators were identified, suggesting a tight regulation, as well as two additional genes involved in capsular polysaccharide biosynthesis (Ent638_4207) and encoding for a glycosyl transferase (Ent638_4208). Cell surface lipopolysaccharides (LPS) have been hypothesized of being involved in host specificity, and the proximity of these genes suggests a collaborative role in plant invasion by *Enterobacter* sp. 638.

The pENT638-1 Plasmid Cellobiose Phosphorylase

On plasmid pENT638-1, the ndvB gene (8532 bp) located next to the plasmid's origin of replication encodes a protein involved in the production of β-(1->2)-glucan. The membrane bound NdvB protein catalyzes three enzymatic activities: the initiation (protein glucosylation), elongation, and cyclization in situ of β-(1->2)-glucan, which is then released into the periplasm.

Example 11

Synergistic Interactions with the Host Plant: Plant Growth Promotion and Health

Indirect Plant Growth Promoting Effects
Nitrogen Fixation and Metabolism

*Enterobacter* sp. 638 is unable to fix nitrogen and lacks the required nif genes. However, it contains the genes required for dissimilatory and assimilatory nitrate reduction pathways. The nitrate transport and nitrate/nitrite reduction genes are present within two operons (narIJHGKXL and nasAB ntrCBA nasR, Ent638_2312-Ent638_2326) separated by an integrase and a putative adhesion/invasion gene. Others regions involved in nitrite transport and reduction (nirBDC, Ent638_3793-3795), nitrate transport and reduction (narUZYWV, Ent638_2061-Ent638_2065), and an ammonium uptake transporter (amtB, Ent638_0919) and its regulator (Ent638_0918), as well as the nitrate/nitrite sensor protein (narQ, Ent638_2964) were also found on its chromosome.

Siderophores

*Enterobacter* sp. 638 has developed an intermediate solution to deal with iron uptake. Its genome contains two ferrous iron uptake systems (FeoAB, EfeUOB) and nine iron ABC transporters.

*Enterobacter* sp. 638 is able to synthesize the siderophore enterobactin (EntD, EntF, EntC, EntE, EntB and EntA), to secrete it (EntS), to recover the iron-enterobactin complex using a ferric siderophore uptake system (ExbDB), and to extract the iron using an enterobactin esterase (Fes) after internalization of the iron-enterobactin complex. The genes involved in this biosynthesis of enterobactin are grouped together with genes encoding two ABC transporters involved in iron uptake (sitABCD and fepCGDB) in a large cluster of 17 genes (Ent638_1111-1128). Furthermore, *Enterobacter* sp. 638 possesses 12 outer membrane ferric and ferric-related siderophore receptors (TonB dependent), which is almost double of the number found in *E. coli* K12 (that only possesses 7 siderophore receptors). This observation is consistent for a bacterium that needs to compete for iron. The presence of an efficient iron uptake system can therefore contribute to protect the host plant against fungal infection.

Antimicrobial Compounds

*Enterobacter* sp. 638 was shown to constitutively produce phenylethylalcohol. This molecule, which is commonly used in perfumery, gives *Enterobacter* sp. 638 a pleasant floral odor, but more interestingly has antimicrobial properties. Two candidate genes (Ent638_1306 and Ent638_1876) encode an enzyme putatively involved in the conversion phenyl-acetaldehyde into phenylethylalcohol. These two genes are located on regions not syntenic with other closely related strains.

4-hydroxybenzoate is a precursor of the important electron carrier ubiquinone, but is also known to have antimicrobial activity. *Enterobacter* sp. 638 possesses the ubiC (Ent638_0243) gene that codes for the putative protein able to perform this reaction.

The *Enterobacter* sp. 638 genome encodes a chloramphenicol acetyltransferase (cat, Ent638_1533) involved in chloramphenicol resistant and that may help the bacteria to be survive against the antimicrobial compounds produced by other endophytic or rhizospheric organisms.

Example 12

Direct Plant Growth Promotion by *Enterobacter* sp. 638

1-aminocyclopropane-1-carboxylate deaminase

The 1-aminocyclopropane-1-carboxylate (ACC) deaminase (acd), (EC: 3.5.99.7) is absent from the *Enterobacter* 638 genome, which confirms previous studies that the strain is unable to metabolize ACC (Taghavi et al. 2009). However, amino acid deaminase was found, but they all lack the particular amino-acids E 296 and L 323 (respectively replaced by a T or S and a T) that approach the pyridine nitrogen atom of PLP in the active site to.

Production of the Roots Growth Promoting Hormones Acetoin, and 2,3-Butanediol

The *Enterobacter* sp. 638 genome carries the gene poxB (Ent638_1387) encoding a pyruvate dehydrogenase. While the principal function of PoxB is to convert pyruvate into acetaldehyde, a small fraction of the pyruvate is converted to acetoin, as a by-product of the hydroxyethyl-thiamin diphosphate reaction intermediate.

The *Enterobacter* sp. 638 genome encodes an acetolactate synthase (budB, Ent638_2027) involved in the conversion of pyruvate to acetolactate. The acetoin decarboxylase (budA, Ent638_2026) catalyzes the conversion of acetolactate into acetoin. Acetoin can be released by the bacteria or subsequently converted into 2,3-butanediol by the acetoin reductase (budC, Ent638_2028) either by *Enterobacter* sp. 638 or by the poplar. Under aerobic condition, acetolactate is spontaneously converted into diacetyl, which in turn can be converted into acetoin by the acetoin dehydrogenase protein (Ent638_2737).

The biosynthesis of volatile compounds by *Enterobacter* sp. 638 and their induction by the addition of poplar leaf extracts was investigated via mass spectrometry. The production of 2,3-butandiol and acetoin was seen for samples containing *Enterobacter* sp. 638 and poplar leaf extract beginning 12 hours after induction (FIG. 8). It should be noted that diacetyl synthesis could not be confirmed, but is likely to occur based on the presence of the complete metabolic pathways for the three compounds. Additional peaks were seen in both the experimental and control samples (6:42, 9:45, and 14:01) and identification of these compounds is currently being performed.

The genome of *Enterobacter* sp. 638 lacks the genes (acoABCX adh) involved in the catabolic conversion of acetoin and 2,3-butanediol to central metabolites. Therefore there is no antagonistic effect between the production and the degradation of these plant growth hormones by *Enterobacter* sp. 638.

Production of the Plant Growth Hormone IAA

The production of indole acetic acid (IAA) by *Enterobacter* sp. 638 was experimentally demonstrated (Taghavi et al. 2009). IAA biosynthesis is likely through the production of indolepyruvate as an intermediate molecule by the tryptophane degradation pathway VII (aromatic amino acid aminotransferase, Ent638_1447). The indolpyruvate decarboxylase IpdC (Ent638_2923) and the putative indole-3-acetaldehyde dehydrogenases (Ent638_0143) further catalyze IAA synthesis.

While there have been described what are presently believed to be the preferred embodiments of the invention, those skilled in the art will realize that changes and modifications may be made thereto without departing from the spirit of the invention, and it is intended to claim all such changes and modifications as full within the true scope of the invention as set forth in the appended claims.

TABLE 1

| traits | *Enterobacter* sp. 638 Chromosome | Plasmid |
|---|---|---|
| size (bp) | 4, 518, 712 | 157, 749 |
| G + C content | 52.98 | 50.57 |
| ORF numbers | 4406 | 152 |
| Assigned function (including putative) | 3457 | 108 |
| Amino acid biosynthesis | 174 | 2 |
| Aromatic amino acid family | 28 | 0 |
| Aspartate family | 44 | 0 |
| Glutamate family | 47 | 1 |
| Pyruvate family | 35 | 1 |
| Serine family | 21 | 0 |
| Histidine family | 11 | 0 |
| Purines, pyrimidines, nucleosides, and nucleotides | 93 | 0 |
| Fatty acid and phospholipid metabolism | 71 | 0 |
| Biosynthesis of cofactors, prosthetic groups, and carriers | 195 | 2 |
| Central intermediary metabolism | 218 | 2 |
| Energy metabolism | 553 | 2 |
| Transport and binding proteins | 631 | 3 |
| Percentage of transporter proteins | 14% | 2% |
| ABC family | 293 | 2 |
| MFS family | 79 | 2 |
| PTS family | 41 | 0 |
| RND family | 14 | 0 |
| Amino acids, peptides and amines | 118 | 0 |
| Anions | 20 | 0 |
| Carbohydrates, organic alcohols, and acids | 106 | 1 |
| Cations and iron carrying compounds | 109 | 1 |
| Nucleosides, purines and pyrimidines | 9 | 0 |
| Porins | 18 | 0 |
| Unknown substrate or drugs | 2 | 0 |
| DNA metabolism | 152 | 4 |
| Transcription | 281 | 4 |
| Protein synthesis | 177 | 0 |
| Protein fate | 188 | 1 |
| Regulatory functions | 515 | 6 |
| two component system | 65 | 3 |
| Cell envelope | 279 | 3 |
| Cellular processes | 457 | 6 |
| Biological processes | 276 | 0 |
| RHS | 2 | 0 |
| Plasmid functions | 7 | 42 |
| putative integrated plasmid | 1 | 0 |
| couple of toxin/anti-toxin | 3 | 7 |
| Prophage functions | 302 | 0 |
| Phage regions | 8 | |

TABLE 2

| Region | From | Ent638_ | to | Ent638_ | size | ORFs | int | tnp | Repeat on ext. | Prophage | tRNA | alternat. codon matrix | Synteny with K12 | Synteny with 341 | Synteny with 568 |
|---|---|---|---|---|---|---|---|---|---|---|---|---|---|---|---|
| 1 | 3756 | 0034 | 83855 | 0066 | 46340 | 35 | – | + | + | | tRNA-Sac | + | – | +/– (*) | +/– (*) |
| 2 | 93676 | 0074 | 103614 | 0086 | 9938 | 13 | – | – | – | | | – | – | – | – |
| 3 | 124182 | 0108 | 132857 | 0114 | 8675 | 7 | – | – | – | | | – | – | – | – |
| 4 | 166537 | 0147 | 169882 | 0148 | 3345 | 3 | – | – | – | | | – | – | + | – |
| 5 | 205544 | 0179 | 212385 | 0183 | 6841 | 8 | – | – | – | | tRNA-Pro | – | – | + | + |
| 6 | 332190 | 283 | 335579 | 286 | 3389 | 18 | – | – | + | | | – | – | – | – |
| 7 | 36414B | 0317 | 373015 | 0321 | 8867 | 5 | – | – | – | | tRNA-Phe | – | – | + | – |
| 8 | 436726 | 0385 | 441897 | 0391 | 5171 | 7 | – | – | – | | | – | – | + | + |
| 9 | 454627 | 0401 | 464073 | 0410 | 9446 | 11 | – | – | – | | | – | +/– | + | + |
| 10 | 477929 | 0423 | 487952 | 0435 | 10023 | 12 | – | – | – | | | – | – | + | – |
| 11 | 523760 | 0463 | 573310 | 0506 | 49550 | 43 | + | – | – | | tRNA-Leu | – | – | + | + |
| 12 | 642565 | 572 | 648283 | 576 | 5718 | 5 | – | – | – | | | + | – | + | +/– |
| 13 | 852653 | 0750 | 860429 | 0756 | 7776 | 7 | – | – | + | | RNA-Asp | + | – | + | – |
| 14a | 376620 | 0770 | 912564 | 820 | 647 | 50 | – | – | + | Phage 1 | tRNA-Thr | + | – | + | – |
| 14b | 912987 | 621 | 035267 | 0637 | 10 | | | | | | | – | – | – | – |
| 15 | 1027052 | 0924 | 1042473 | 0937 | 15421 | 15 | – | – | – | | | + | +/– | + | +/– |
| 16a | 1107864 | 0996 | 1154361 | 1055 | 46497 | 59 | + | – | – | Phage 2 | tRNA-Arg | + | – | + | + |
| 16b | 1164789 | 1056 | 1223024 | 1114 | 68235 | 66 | – | – | – | | | – | – | – | – (*) |
| 17 | 1248443 | 1135 | 1258304 | 1143 | 9861 | 8 | – | – | – | | | + | – | + | + |
| 18 | 1386002 | 1260 | 1392280 | 1264 | 6278 | 5 | – | – | + | | | + | +/– | + | +/– |
| 19 | 1433737 | 1306 | 1438417 | 1309 | 4680 | 5 | – | – | + | | | + | – | + | + |
| 20 | 1441382 | 1312 | 1446428 | 1314 | 5046 | 3 | – | – | + | Phage 3 | tRNA (rybB) | + | – | + | + |
| 21 | 1472316 | 1338 | 1492323 | 1361 | 20007 | 23 | + | – | – | | | + | – | – | – |
| 22 | 1533390 | 1400 | 1544126 | 1406 | 10736 | 7 | – | – | + | | tRNA-Ser | + | – | +/– (*) | – |
| 23 | 1639354 | 1484 | 1691939 | 1538 | 52585 | 29 | + | – | + | Phage 4 | | +/– | – | – | – (*) |
| 24 | 1804662 | 1660 | 1812852 | 1661 | 8190 | 12 | + | – | – | | | + | – | + | + |
| 25 | 1886255 | 1737 | 1892165 | 1742 | 5910 | 6 | – | – | – | | tRNA-Val | – | – | + | +/– (*) |
| 26 | 1929035 | 1775 | 1937050 | 1781 | 8015 | 7 | – | – | – | | | + | – | – | +/– |
| 27 | 2000083 | 1841 | 2001815 | 1843 | 1732 | 4 | + | – | – | | | + | – | + | + |
| 28 | 2015509 | 1858 | 2072420 | 1909 | 56911 | 51 | – | – | – | Phage 5 | | + | – | – | – |
| 29 | 2115297 | 1949 | 2225046 | 2051 | 109749 | 103 | – | – | + | | | – | – | + | + |
| 30 | 2260061 | 2081 | 2272628 | 2096 | 12567 | 16 | – | – | + | | | + | +/– | + | +/– |
| 31 | 2285577 | 2108 | 2302826 | 2119 | 17249 | 12 | + | – | – | | | – | +/– | + | +/– (*) |
| 32a | 2405497 | 2214 | 2451788 | 2269 | 65162 | 55 | + | – | + | Phage 6 | | – | – | – | – |
| 32b | 2451959 | 2270 | 2470659 | 2294 | 15098 | 24 | – | – | – | | tRNA-Asn | + | – | – | – |
| 33 | 2504012 | 2320 | 2519110 | 2329 | 15098 | 10 | + | – | + | | | + | – | + | + |
| 34 | 2534142 | 2346 | 2547263 | 2356 | 13121 | 11 | – | – | + | | | + | – | – | – |
| 35 | 2652901 | 2458 | 2661174 | 2464 | 8273 | 7 | – | – | – | | | + | – | + | + |
| 36 | 2706828 | 2510 | 2720695 | 2521 | 13867 | 12 | – | – | – | | | + | – | + | + |
| 37a | 2747355 | 2553 | 2783747 | 2578 | 36392 | 25 | + | – | + | | | + | – | + | + |
| 37b | 2784850 | 2570 | 2824258 | 2626 | 39408 | 49 | + | – | + | | | – | – | + | + |
| 38 | 2847062 | 2647 | 2851589 | 2650 | 4527 | 4 | – | – | – | | | – | – | + | + |
| 39 | 2902726 | 2690 | 2935856 | 2719 | 33130 | 30 | + | – | – | | | + | – | + | – |
| 40 | 3125655 | 2887 | 3162212 | 2916 | 36557 | 30 | – | – | – | | tRNA-Arg | + | – | + | +/– (*) |
| 41 | 3236067 | 2980 | 3241398 | 2983 | 5331 | 4 | + | + | – | | | + | – | + | – |
| 42 | 3253890 | 2994 | 3259362 | 2997 | 5472 | 4 | – | – | – | | | – | – | + | – |

TABLE 2-continued

| | | | | | | | | | | | | | | |
|---|---|---|---|---|---|---|---|---|---|---|---|---|---|---|
| 43a | 3375316 | 3101 | 3420151 | 3112 | 3386009 | 11 | + | — | — | — | Phage 7 | tmRNA | +/— | |
| 43b | 3386662 | 3113 | 3429862 | 3146 | 43170 | 15 | — | — | — | — | — | — | — | |
| 44 | 3460156 | 3176 | 3462550 | 3178 | 2394 | 3 | — | — | — | + | — | — | + | |
| 45 | 3491626 | 3205 | 3495685 | 3208 | 4059 | 4 | — | — | — | + | — | — | +/— | |
| 46 | 3581959 | 3279 | 3586075 | 3282 | 4116 | 4 | — | — | — | + | — | — | + | |
| 47 | 3590526 | 3287 | 3609775 | 3305 | 19240 | 19 | + | — | — | + | + | tRNA-Gly | +/— | (*) |
| 48 | 3688251 | 3384 | 3715198 | 3408 | 26947 | 25 | — | — | — | + | — | tRNA-Phe | — | |
| 49 | 3738015 | 3433 | 3750557 | 3442 | 12542 | 10 | — | — | — | +/— (*) | — | — | — | |
| 50 | 3772076 | 3463 | 3777014 | 3469 | 4938 | 7 | + | — | — | + | — | — | — | |
| 51a | 3783633 | 3475 | 3814474 | 3514 | 30841 | 39 | + | — | — | — | + | Phage 8 | tRNA-Met | — (*) |
| 51b | 3814471 | 3516 | 3832226 | 3530 | 17755 | 24 | — | — | — | — | — | — | — | |
| 52 | 4069288 | 3771 | 4076336 | 3779 | 7048 | 9 | — | — | — | + | — | — | + | (*) |
| 53 | 4192604 | 3882 | 4212209 | 3905 | 19605 | 24 | + | — | — | + | — | — | + | (*) |
| 54 | 4255568 | 3936 | 4269242 | 3944 | 13674 | 9 | — | — | — | + | — | — | — | |
| 55 | 4294762 | 3964 | 4298896 | 3966 | 4134 | 3 | — | — | — | + | — | — | + | |
| 56 | 4425327 | 4070 | 4437770 | 4081 | 12443 | 12 | — | — | — | + | — | — | — | (*) |
| | | | | | | 495 | | | | | | | | |

| Region | Gene content | Presence in (*) | Remarks/additional observations |
|---|---|---|---|
| 1 | transporter for sugar uptake (PTS lactose family), Beta-glucosidase (conversion of cellobiose into glucose or glucoside into glucose), filamentous haemagglutinin, transporter (MFS family), Predicted Zn-dependent hydrolases, ORFs of unknown function | transporter for sugar uptake (PTS lactose family), Beta-glucosidase (conversion of unknown cellobiose into glucose or glucoside into glucose), filamentous haemagglutinin | |
| 2 | Fimbriae biosynthesis | | |
| 3 | Putative membrane-associated metal-dependent hydrolase, Glycosyltransferase | | inside a waa operon |
| 4 | Hemolysin activation/secretion protein | | |
| 5 | Rhs, peptidoglycan-binding (LysM), several partial duplication | Rhs | |
| 6 | Fructokinase, fructose biphosphate aldolase | | |
| 7 | Nickel chelation for uptake or usage as cofactor, Outer membrane autotransporter with Pectin lyase fold/virulence factor (adhesin) | | |
| 8 | Regulator, FMN-dependent NADH-azoreductase 2, Protein of unknown function, Antibiotic resistance | | |
| 9 | Fimbriae biosynthesis for adhesion/virulence, genes duplicated | | dowstream of this region an Integral membrane sensor hybrid histidine kinase precursor Is absent from the K12 genome |
| 10 | Cytochrome, regulator, unknown function, dihydroorotase (peptidase), putative selenocysteine synthase L-seryl-tRNA(Ser) selenium transferase (Pyridoxal phosphate-dependent) | | |
| 11 | Integrase, phage protein, DNA repair (Dnd proteins), plasmid stabilization system, pectate lyase, oligogalacturonate-specific porin (KdgM), protease, possible anti-oxydant, regulators, autotransporter/filamentous haemagglutinin/adhesin, regulator, transcriptionnal regulator involved in virulence, system de secretion, possibly secretion of virulence factor | | |

TABLE 2-continued

| | | |
|---|---|---|
| 12 | Iron-hydroxymate transporter (MFS and ABC family) | |
| 13 | Regulator, ABC transporter for amino acids | |
| 14a | Integrase, phage proteins | |
| 14b | Transduction with Phage 1: alpha/beta hydrolase, fimbrial protein, amino acid transporter, methylatransferase, two component sensor/regulator, permease, S-methylmethionine transporter, S-methylmethionine: homocysteine methyltransferase, haemolysin co-regulated protein (HCP), ferric ABC transporter (syntenic with K12), integrase | the synteny is broken but the genes from this region are present on the K12, 342 and 568 genomes |
| 15 | Regulator, lactose degradation (syntenic with K12), signal transduction (domain EAL), transporter (beta-glucoside PTS family) | |
| 16a | Phage integrase, phage proteins | |
| 16b | Transduction with Phage 2: Putative TonB-dependent siderophore receptor, phenylalanine transporter, Nucleoside: H+ symporter, Transcriptional regulator (LacI, XRE, TetR, LysR, GntR), permease (MFS family), fimbriae, dihydropteridine reductase, metallo-hydrolase/oxidoreductase, Ferrichrysobactin TonB-dependent siderophore receptor, Enterochelin esterase, P-type ATPase transporter, RND transporter, Ribosomal large subunit pseudouridine synthase A, Putative cold-shock DNA-binding domain protein, TonB-dependent receptor, ABC transporter for amino acids, GCN5-related N-acetyltransferase, ABC transporter for chelated iron (SitABCD) | |
| 17 | ABC transporter Ribose uptake, ribose kinase, Methionine metabolism | |
| 18 | Histidine degradation (hutIGCUH) | |
| 19 | Aldoketo-oxidoreductase, Glycoside hydrolase (family 1), Transporter (PTS lactose/cellobiose family, IIC subunit), Transcriptional regulator (GntR) | |
| 20 | Alpha-glucosidases (glycosyl hydrolases family 31), Hexuronate transporter, Periplasmic binding protein/LacI transcriptional regulator | |
| 21 | Putative Fucose 4-O-acetylase and related acetyltransferases, phage proteins, putative TonB-dependent siderophore receptor | Cyclopropane-fatty-acyl-phospholipid synthase, Amine oxidase encoded on the 342 genome |
| 22 | Crispr associated protein | The flanking region (Ent638_1145-1152) coding alkyl hydroperoxide reductase (F52a subunit), chloride peroxide, and ribonuclease were found on 342 but not on 568 and partially on the K12 genome. |
| 23 | Cyclopropane-fatty-acyl-phospholipid synthase, Amine oxidase, transporter (MFS), transcriptional regulator, Glycosyltransferase, Methionine aminopeptidase (MAP) (Peptidase M), arylsulfatase: sulfur metabolism, alternative pyrimidine degradation pathway, autotransporter/Filamentous haemagglutinin/Adhesin (fragments), IS transposase (family IS110), Chloramphenicol acetyltransferase (CAT), alternative pyrimidine degradation pathway | The pyrimidine degradation pathway is present of the genome of the three bacteria 342, 568 and K12. Next to this region (Ent 1551-1562), 342 and 568 lack a region encoding for the production of curli |

TABLE 2-continued

| | | |
|---|---|---|
| 24 | Phage proteins | The gene (regulators and diguanylate cyclase) flanking region 24 (Ent638_1688-1669) are absent in 568. The region Ent638_1584-1597 involved in flagellar biosynthesis is lacking in 342 (flgNMABCDEFGHIJKL). The genes Ent638_1688-1695 (phosphatidyl transferase, ABC thiosulfate sulfur transporter and thiosulfate sulfur transferase) are absent from the 568 genome. |
| 25 | TonB-dependent heme/hemoglobin receptor family protein for iron uptake | |
| 26 | Autotransporter for adhesion, ABC transporter system for amino acid/glutamine uptake, Putative metal-dependent RNase, consists of a metallo-beta-lactamase domain and an RNA-binding KH domain, carbonic anhydrase | The genome of 342 and 568 contain the ABC transporter system for amino acid/glutamine uptake genes from this region. |
| 27 | Phage integrase (fragment), incomplete phage inserted into a two component sensor/regulator (RstAB) | |
| 28 | Chemotaxis/mobility?, Autotransporter adhesin/invasin-like protein (YadA), Antibiotic biosynthesis, RND efflux system nodulation?, RND efflux system drug resistance, Unknown function but small possible legume lectin, beta domain for attachment, MFS transporter, lysophospholipase, coagulase/fibrinolysin, Phage regulator, SOS response | |
| 29 | RND transporter, Pectin acetylesterase, Many gene involved in amino acid transport, Many transcriptional regulator, Putative IAA acetyltransferase, sucrose/fructose utilisation with PTS from the beta-glc family, synthesis of acetoin, periplasmic disulfide isomerase/thiol-disulphide oxidase (DsbG), depolymerisation of alginates, many transporters and many regulators | possibly not an island but acquisition of many gene (compared with K12) during Endophytic evolution |
| 30 | Glutamate ABC transporter, Amino acid ABC transporter, Chemotaxis: aerotaxis | possibly not an island but acquisition of many gene |
| 31 | Virulence proteins SrfA, methionine synthase, Polygalacturonase, pectate lyase (secreted), chondroitin AC/alginate lyase, together with pectate lyase important for colonisation (secreted), putative hydrolase (secreted), Transcriptional regulator, Chemiotaxis: aerotaxis | presence of the srfABC genes on the 568 genome |
| 32a | Phage, phange integrase | |
| 32b | Transduction with Phage 6: GCN5-related N-acetyltransferase, Transcriptional regulator (TetR), N-ethylmaleimide reductase, Oxidoreductase, permease/transporter, dehydrogenase, putative intracellular septation protein involved in cell division, hydrolase, membrane spanning TonB, 2-dehydropantoate, Putative drug/metabolite exporter (DMT family), | |
| 33 | Integrase, nitrate reductase (NasA), nitrate reductase (NasB), nitrate transport (NrtCBA), region flanked by the nar operon involved in nitrate reduction and nitrate/nitrite transport | Presence of the entire region except the integrace gene |

TABLE 2-continued

| | | |
|---|---|---|
| 34 | oxidoreductase, Amino acid ABC transporter, purine ribonuclease efflux, trehalose degradation), tonB-dependent siderophore integrase, fimbria/pili (located next to chemotaxis genes and fimbria genes) | |
| 35 | | 342 is also lacking the flanking region coding gened involved in fimbrial biosynthesis |
| | | 568 genomes are lacking the region Ent638_2477-2490 encoding genes for an intracellular protease/amidase, a ferritin-like protein, an anaerobic C4-dicarboxylate transporter, a transporter (MFS family), a putative Ribose/galactose isomerase, a putative metal-dependent phospholydrolase, another ferritin iron storage protein, a tyrosine transporter and several conserved protein of unknown function. Some of these genes are also absent in K12. |
| 36 | Acyl-CoA reductase (LuxC) and Acyl-protein synthetase (LuxE) which are substrat for light production by luciferase, Transketolase, fatty acid biosynthesis | Next to a large region of flagelle encoding genes fli which is lacking in 342. |
| 37a | Transduction with Phage 7: Outer membrane protein N,N-acetylmuramic acid 6-phosphate etherase, Two-component sensor/regulator, Thiamine biosynthesis lipoprotein, Putative NADH: flavin oxidoreductase, Tartrate transporter, anaerobic class I fumarate hydratase, regulators (for cysteine biosynthesis and nitrogen assimilation), P1-type ATPase, Universal stress protein G, transporter (RND), Putative acyltransferases, palm fioyl transferase for Lipid A, shikimate transporter, AMP nucleosidase, Aminopeptidase P, four tRNA-Asn locus, DNA gyrase inhibitor D-alanyl-D-alanine carboxypeptidase | |
| 37b | Phage integrase, phage proteins | |
| 38 | LPS biosynthesis | Most of the flanking region from Ent638_2645 to Ent638_2672 involved in LPS biosynthesis are absent from the 342 and 568 genomes but present in K12 |
| 39 | glutathione peroxidase, phosphorilation of lipid, amino acid ABC transporter, diaminobutyrate catabolism, tyrosine kinase, phosphatase | presence of amino acid ABC transporter, diaminobutyrate catabolism in the 342 and 568 genomes |
| 40 | Putative integrated plasmid: phage integrase, plasmid function, phage integrase, surface reorganisation resulting in increased adherence and increased conjugation | Putative integrated plasmid |
| 41 | Transposase (IS481), Asparaginase, leucyl amidopeptidase | |
| 42 | Transcriptional regulator, MFS transporter, beta-xylosidase, Xyloside transporter | |
| 43a | Phage integrase, endonuclease, phage protein (uncomplete phage) | Transduction with the phage? |
| 43b | Transduction with Phage 8: Kinase, Sigma/anti-sigma factor, Putative hemagglutinin/hemolysin protein, Hemagglutinin transporter (outer | The gene encoding for non-haem manganese-containing catalase rpoS-dependent (KatN), Cytochtome db ubiquinol oxidase, subunit I & |

TABLE 2-continued

| | | |
|---|---|---|
| | membrane protein, ABC permease, MFP), putative 2-aminoadipate transaminase, non-haem manganese-containing catalase rpoS-dependent (KatN), Cytochrome bd ubiquinol oxidase, subunit I & II, competence damage-inducible protein A, virulence membrane protein (PagC), Transcriptional regulator (LysR), Short-chain dehydrogenase/reductase, Methyltransferase type 11, putative deaminase/amidohydrolase with metallo-dependent hydrolase domain, putative carbamate kinase, Xanthine/uracil/vitamin C permease, putative DNA-binding transcriptional regulator | II, competence damage-inducible protein A are present on the 342 genome. |
| 44 | ABC transporter | |
| 45 | ABC transporter involved in Fe3+ transport (EitABCD) | |
| 46 | GCN4-N-acetyltransferase, transcriptional regulator, 6-P-beta-glucidase, Transporter (PTS lactose/cellobiose family), regulator lacI-like | |
| 47 | Pectin degradation protein, transposase family IS481, ABC transporter (possibly for sugar with a specialisation in pectin transport) (TogMNAB), Pectin degradation, Oligogalacturonate-specific porin precursor (product of pectin degradation), Regulator | Except the genes Ent638_3288: the IS element (IS481 family), and Ent638_3293 encoding the oligogalacturonide lyase. The genome of 568 doesn't encode the proteins involved in pectin degradation. |
| 48 | Autransporter with adhesin domain, antioxidant, Molybdenum ABC transporter, Iron ABC-transport protein, periplasmic-binding component, Mechanosensitive ion channel, Chemiotaxis regulator, Autransporter with a Serine-rich adhesin domain | |
| 49 | Sugar transporter (MFS), Iron compound-binding protein of ABC transporter family, periplasmic component (iron-enterobactin transporter), Ton B-dependent siderophore receptor | 342 genome lacks Ent638_3433-3436 (unsaturated glucuronyl hydrolase, oligosaccharide/H+ symporter, a conserved protein of unknown function and a transcriptional regulator (AraC family) |
| 50 | Urease (ureDABCEFG) | |
| 51a | Phage integrase, phage proteins (conserved in *K. pneumoniae, E. coli* UTI89) | some of the phage genes are syntenic with 568. |
| 51b | Transduction with Phage 9: | |
| 52 | Phosphatidylglycerol-membrane-oligosaccharide glycerophosphotransferase, Transcriptional regulators (LysR, TetR, XRE), Metallo hydrolase, putative mRNA endoribonuclease, heat protein (DnaJ), siderophore, fused signal transducer for aerotaxis sensory, putrescine: 2-oxoglutaric acid aminotransferase Malonate (mdc genes), Malonate transporter (family of auxin efflux carrier) (MdcF) | |
| 53 | Fatty acid biosynthesis | Except the genes Ent638_3900-3905 encoding a 4'-phosphopantetheinyl transferase (acpT), a Ent638_3658-3662: salicylic acid transporter, putative N-acetylmannosamide kinase and N-acetylneuraminate lyase and the regulator (nanKTAR) are absent on the genome of 342 and 568 |

TABLE 2-continued

| | | |
|---|---|---|
| | | short-chain dehydrogenase/reductase SDR precursor, a NLP/P60 protein precursor (similar to putative Cell wall-associated hydrolases (invasion-associated proteins), a HAD-superfamily hydrolase, subfamily IB (PSPase-like), a tellurium resistance protein (terC), and an Ion transport 2 protein |
| 54 | Cellulose biosynthesis (bcsZDCBA) | |
| 55 | Transporter (Beta-glucoside PTS family) | |
| 56 | Ribose ABC transporter, raffinose operon (transport/utilisation) | In addition, 568 lacks the flanking region Ent638_4064-4070 encoding the rhaTRSBADBA (L-rhamnose:proton symporter, DNA-binding transcriptional activator, L-rhamnose-binding, DNA-binding transcriptional activator, L-rhamnose-binding, rhamnulokinase, L-rhamnose isomerase, rhamnulose-1-phosphate aldolase, D-ribose ABC transporter, periplasmic rhamnose-binding protein precursor, Ribose import ATP-binding protein rbsA 1) |

The coordinate given are those of the genes, not those of the repeat from phage organism used for the comparison: *K. pneumoniae* MGH78578, *E. coli* K12, O157-H7, UTI89, *C. koseri* BAA-895
Compared with 568 and 342, K12 and 638 have the operons/0231-0234 porins and lipoproteins;

TABLE S1

(PRIMERS)

| Locus | Gene | Sequence | Tm |
|---|---|---|---|
| Ent638_2025 | budRf | TATTCCCGCAGGAGATTGCT | 58 |
| Ent638_2025 | budRr | AAGCTGTGACGACTGCAACATATT | 59 |
| Ent638_2026 | budAf | GGCGAAATGATTGCCTTCAG | 59 |
| Ent638_2026 | budAr | CCAGGTCATTACTGCGAAAGGT | 59 |
| Ent638_2027 | budBf | ACAGCCCCGTTGAATACGAA | 59 |
| Ent638_2027 | budBr | GGGCACATAGTTGCGTTCTTC | 58 |

TABLE S1-continued (PRIMERS)

| Locus | Gene | Sequence | Tm |
|---|---|---|---|
| Ent638_2028 | budCf | TTTGCGGCAGTGGAGAAAG | 59 |
| Ent638_2028 | budCr | TGGCGTGATCGACTCAATTG | 59 |
| Ent638_4249 | repAf | TAGCAAGAAAACAGGCGACAAGT | 59 |
| Ent638_4249 | repAr | GCAGTCGCTCATCAGCTTGA | 59 |
| Ent638_R0104 | 16Sf | AGTGATTGACGTTACTCGCAGAAG | 59 |
| Ent638_R0104 | 16Sr | TTTACGCCCAGTAATTCCGATT | 59 |

TABLE S4

Microarrays

| SEQ_ID_s | Fold Change (Rich/Poor) | p value (FDR) | T statistic | FUNCTION | COGclassID | ClassDescription |
|---|---|---|---|---|---|---|
| Ent638_0190 | 2.127 | 0.0263 | 10.447 | protein chain elongation factor EF-Tu (duplicate of tufA) | J | Translation, ribosomal structure and biogenesis |
| Ent638_0194 | 2.453 | 0.0257 | 11.518 | 50S ribosomal subunit protein L1 | J | Translation, ribosomal structure and biogenesis |
| Ent638_0195 | 3.1 | 0.0837 | 3.807 | 50S ribosomal subunit protein L10 | J | Translation, ribosomal structure and biogenesis |
| Ent638_0197 | 2.372 | 0.0269 | 10.192 | RNA polymerase, beta subunit | K | Transcription |
| Ent638_0200 | 2.687 | 0.0242 | 13.404 | Phosphotransferase system, lactose/cellobiose-specific IIB subunit | G | Carbohydrate transport and metabolism |
| Ent638_0213 | 3.284 | 0.133 | 2.85 | HU, DNA-binding transcriptional regulator, alpha subunit | T | Signal transduction mechanisms |
| Ent638_0238 | 2.351 | 0.0202 | 17.811 | maltose transporter subunit; periplasmic-binding component of ABC superfamily | G | Carbohydrate transport and metabolism |
| Ent638_0241 | 6.748 | 0.00954 | 58.758 | maltose outer membrane porin (maltoporin) | G | Carbohydrate transport and metabolism |
| Ent638_0285 | 2.719 | 0.0369 | 7.441 | Fructose-bisphosphate aldolase 1 | G | Carbohydrate transport and metabolism |
| Ent638_0286 | 2.061 | 0.0767 | 4.042 | Putative ABC-type sugar transport system, auxiliary component | R | General function prediction only |
| Ent638_0287 | 4.625 | 0.0166 | 22.815 | Periplasmic ribose-binding protein of ABC transport system | G | Carbohydrate transport and metabolism |
| Ent638_0326 | 8.129 | 0.018 | 35.517 | aspartate ammonia-lyase | C; E | Energy production and conversion; Amino acid transport and metabolism |
| Ent638_0449 | 3.34 | 0.066 | 4.515 | Putative C4-dicarboxylate anaerobic carrier precursor | R | General function prediction only |
| Ent638_0450 | 3.464 | 0.0439 | 6.095 | Ornithine carbamoyltransferase 1 (OTCase 1) | F | Nucleotide transport and metabolism |

TABLE S4-continued

| | Microarrays | | | | | |
|---|---|---|---|---|---|---|
| SEQ_ID_s | Fold Change (Rich/ Poor) | p value (FDR) | T statistic | FUNCTION | COGclassID | ClassDescription |
| Ent638_0451 | 4.851 | 0.0779 | 4.01 | Carbamate kinase | E | Amino acid transport and metabolism |
| Ent638_0452 | 4.792 | 0.0298 | 9.144 | Arginine deiminase (ADI) (Arginine dihydrolase) (AD) | E | Amino acid transport and metabolism |
| Ent638_0641 | 2.63 | 0.0294 | 9.327 | GTP-binding tubulin-like cell division protein | D | Cell cycle control, cell division, chromosome partitioning |
| Ent638_0660 | 3.804 | 0.0179 | 29.044 | pyruvate dehydrogenase, decarboxylase component E1, thiamin-binding | C; G | Energy production and conversion; Carbohydrate transport and metabolism |
| Ent638_0662 | 4.208 | 0.000915 | 219.599 | lipoamide dehydrogenase, E3 component is part of three enzyme complexes | C | Energy production and conversion |
| Ent638_0665 | 3.576 | 0.0247 | 13.073 | bifunctional aconitate hydratase 2 and 2-methylisocitrate dehydratase | C; E | Energy production and conversion; Amino acid transport and metabolism |
| Ent638_0685 | 2.019 | 0.0799 | 3.932 | DNA-binding transcriptional regulator of rRNA transcription, DnaK suppressor protein | T | Signal transduction mechanisms |
| Ent638_0716 | 2.254 | 0.0262 | 10.425 | periplasmic chaperone | M | Cell wall/membrane/ envelope biogenesis |
| Ent638_0759 | 2.044 | 0.0348 | 7.757 | D-sedoheptulose 7-phosphate isomerase | G; M | Carbohydrate transport and metabolism; Cell wall/membrane/ envelope biogenesis |
| Ent638_0896 | 2.304 | 0.0289 | 9.511 | cytochrome o ubiquinol oxidase subunit IV | C | Energy production and conversion |
| Ent638_0897 | 3.49 | 0.0506 | 5.52 | cytochrome o ubiquinol oxidase subunit III | C | Energy production and conversion |
| Ent638_0898 | 2.487 | 0.103 | 3.372 | cytochrome o ubiquinol oxidase subunit I | C | Energy production and conversion |
| Ent638_0899 | 3.03 | 0.0151 | 27.174 | cytochrome o ubiquinol oxidase subunit II | C | Energy production and conversion |
| Ent638_0903 | 2.094 | 0.00815 | 50.908 | peptidyl-prolyl cis/trans isomerase (trigger factor) | O | Posttranslational modification, protein turnover, chaperones |
| Ent638_0987 | 2.028 | 0.024 | 12.433 | Type-1 fimbrial protein, A chain precursor (Type-1A pilin) | N; U | Cell motility; Intracellular trafficking, secretion, and vesicular transport |
| Ent638_1050 | −2.041 | 0.0481 | −5.699 | hypothetical protein of unknown function | S | Function unknown |
| Ent638_1053 | −2.279 | 0.0484 | −5.665 | Lipolytic enzyme, G-D-S-L family precursor | R | General function prediction only |
| Ent638_1182 | 3.201 | 0.0161 | 24.254 | glutamate and aspartate transporter subunit; periplasmic-binding component of ABC superfamily | E; T | Amino acid transport and metabolism; Signal transduction mechanisms |

TABLE S4-continued

Microarrays

| SEQ_ID_s | Fold Change (Rich/Poor) | p value (FDR) | T statistic | FUNCTION | COGclassID | ClassDescription |
|---|---|---|---|---|---|---|
| Ent638_1204 | 2.631 | 0.0184 | 20.459 | putrescine/proton symporter: putrescine/ornithine antiporter | E | Amino acid transport and metabolism |
| Ent638_1205 | 4.027 | 0.0258 | 10.764 | ornithine decarboxylase isozyme, inducible | E | Amino acid transport and metabolism |
| Ent638_1221 | 2.03 | 0.0244 | 12.635 | citrate synthase | C | Energy production and conversion |
| Ent638_1224 | 2.59 | 0.024 | 12.596 | succinate dehydrogenase, flavoprotein subunit | C | Energy production and conversion |
| Ent638_1226 | 5.448 | 0.0244 | 13.456 | 2-oxoglutarate decarboxylase, thiamin-requiring | C | Energy production and conversion |
| Ent638_1227 | 4.206 | 0.0309 | 8.724 | dihydrolipoyltranssuccinase | C; I | Energy production and conversion; Lipid transport and metabolism |
| Ent638_1228 | 2.918 | 0.0417 | 6.508 | succinyl-CoA synthetase, beta subunit | C | Energy production and conversion |
| Ent638_1229 | 4.423 | 0.0171 | 23.421 | succinyl-CoA synthetase, NAD(P)-binding, alpha subunit | C | Energy production and conversion |
| Ent638_1231 | 2.735 | 0.0329 | 8.087 | cytochrome d terminal oxidase, subunit II | C | Energy production and conversion |
| Ent638_1263 | 3.27 | 0.116 | 3.114 | Urocanate hydratase (Urocanase) (Imidazolonepropionate hydrolase) | C | Energy production and conversion |
| Ent638_1298 | 2.106 | 0.0633 | 4.648 | glutamine transporter subunit; periplasmic binding component of ABC superfamily | E; T | Amino acid transport and metabolism; Signal transduction mechanisms |
| Ent638_1338 | −3.102 | 0.0533 | −5.307 | Putative Fucose 4-O-acetylase and related acetyltransferases | G | Carbohydrate transport and metabolism |
| Ent638_1341 | −2.111 | 0.0583 | −4.928 | conserved hypothetical phage exported protein of unknown function | D; L; N; T | Cell cycle control, cell division, chromosome partitioning; Replication, recombination and repair; Cell motility; Signal transduction mechanisms |
| Ent638_1430 | 2.324 | 0.0436 | 6.138 | 30S ribosomal subunit protein S1 | J | Translation, ribosomal structure and biogenesis |
| Ent638_1469 | 2.039 | 0.0254 | 11.293 | outer membrane protein A (3a; II*; G; d) | M | Cell wall/membrane/envelope biogenesis |
| Ent638_1490 | 3.067 | 0.15 | 2.63 | Putative oxidoreductase, short-chain dehydrogenase/reductase family | R | General function prediction only |
| Ent638_1499 | −2.164 | 0.0429 | −6.238 | Glycosyltransferase | G | Carbohydrate transport and metabolism |
| Ent638_1514 | 3.223 | 0.0191 | 19.678 | glucose-1-phosphatase/inositol phosphatase | G | Carbohydrate transport and metabolism |
| Ent638_1526 | −2.828 | 0.0203 | −18.472 | Putative autotransporter | U | Intracellular trafficking, |

TABLE S4-continued

| | Microarrays | | | | | |
|---|---|---|---|---|---|---|
| SEQ_ID_s | Fold Change (Rich/ Poor) | p value (FDR) | T statistic | FUNCTION | COGclassID | ClassDescription |
| | | | | protein (fragment) | | secretion, and vesicular transport |
| Ent638_1587 | 3.209 | 0.0163 | 22.337 | flagellar component of cell-proximal portion of basal-body rod | N | Cell motility |
| Ent638_1588 | 5.216 | 0.0263 | 10.4 | flagellar component of cell-proximal portion of basal-body rod | N | Cell motility |
| Ent638_1589 | 3.559 | 0.0167 | 24.377 | flagellar hook assembly protein | N | Cell motility |
| Ent638_1590 | 3.744 | 0.0255 | 11.515 | flagellar hook protein | N | Cell motility |
| Ent638_1591 | 2.479 | 0.0333 | 7.975 | flagellar component of cell-proximal portion of basal-body rod | N | Cell motility |
| Ent638_1596 | 2.019 | 0.149 | 2.64 | flagellar hook-filament junction protein 1 | N; T | Cell motility; Signal transduction mechanisms |
| Ent638_1597 | 2.902 | 0.0555 | 5.128 | flagellar hook-filament junction protein | N | Cell motility |
| Ent638_1656 | −2.303 | 0.0245 | −12.219 | Virulence protein msgA | R | General function prediction only |
| Ent638_1657 | −2.183 | 0.0554 | −5.161 | Methyl-accepting chemotaxis sensory transducer | N; T | Cell motility; Signal transduction mechanisms |
| Ent638_1724 | 2.288 | 0.0974 | 3.474 | threonyl-tRNA synthetase | J | Translation, ribosomal structure and biogenesis |
| Ent638_1725 | 2.256 | 0.111 | 3.214 | Bacterial translation initiation factor 3 (BIF-3) | J | Translation, ribosomal structure and biogenesis |
| Ent638_1750 | 2.083 | 0.0467 | 5.875 | Formate dehydrogenase, nitrate-inducible, major subunit | C | Energy production and conversion |
| Ent638_1755 | −2.084 | 0.0612 | −4.785 | Hypothetical protein of unknown function | S | Function unknown |
| Ent638_1773 | −2.188 | 0.0251 | −10.953 | DL-methionine transporter subunit; periplasmic-binding component of ABC superfamily | P | Inorganic ion transport and metabolism |
| Ent638_1804 | −2.004 | 0.0317 | −8.356 | conserved protein of unknown function | S | Function unknown |
| Ent638_1841 | −2.107 | 0.0415 | −6.448 | Putative lambdoid prophage Rac integrase (fragment) | L | Replication, recombination and repair |
| Ent638_1856 | −2.048 | 0.0317 | −8.405 | fragment of DNA-binding transcriptional regulator (part 2) | T | Signal transduction mechanisms |
| Ent638_1903 | −2.118 | 0.0224 | −15.399 | Hypothetical protein of unknown function | S | Function unknown |
| Ent638_1915 | −2.007 | 0.0294 | −9.325 | Acid shock protein precursor | R | General function prediction only |
| Ent638_1941 | −2.307 | 0.025 | −13.516 | Hypothetical exported protein of unknown function | S | Function unknown |
| Ent638_2031 | −2.058 | 0.0382 | −7.016 | Periplasmic disulfide isomerase/thiol-disulphide oxidase | O | Posttranslational modification, protein turnover, chaperones |
| Ent638_2051 | −2.094 | 0.0432 | −6.201 | Putative polyphosphate kinase | F | Nucleotide transport and metabolism |

TABLE S4-continued

| | Microarrays | | | | | |
|---|---|---|---|---|---|---|
| SEQ_ID_s | Fold Change (Rich/Poor) | p value (FDR) | T statistic | FUNCTION | COGclassID | ClassDescription |
| Ent638_2057 | 2.542 | 0.0477 | 5.757 | Outer membrane porin protein | M | Cell wall/membrane/envelope biogenesis |
| Ent638_2166 | −2.293 | 0.0395 | −6.835 | peripheral inner membrane phage-shock protein | R | General function prediction only |
| Ent638_2210 | −2.647 | 0.0248 | −11.137 | fragment of conserved protein of unknown function (part 2) | S | Function unknown |
| Ent638_2218 | −2.072 | 0.0248 | −11.07 | Phage protein | — | — |
| Ent638_2221 | −2.12 | 0.0237 | −14.041 | Putative phage lipoprotein | — | — |
| Ent638_2243 | −2.466 | 0.0268 | −10.246 | conserved protein of unknown function | S | Function unknown |
| Ent638_2246 | −2.359 | 0.0353 | −7.673 | Hypothetical protein of unknown function | S | Function unknown |
| Ent638_2250 | −2.339 | 0.0879 | −3.692 | Phage DNA methylase N-4/N-6 domain protein | L | Replication, recombination and repair |
| Ent638_2256 | −3.509 | 0.0169 | −23.668 | Phage DNA-damage-inducible protein I | — | — |
| Ent638_2269 | −2.086 | 0.0247 | −13.482 | Prophage lambda integrase (Int(Lambda)) (Prophage e14 integrase) | L | Replication, recombination and repair |
| Ent638_2281 | −2.145 | 0.024 | −12.802 | Alcohol dehydrogenase, zinc-binding domain protein | C | Energy production and conversion |
| Ent638_2282 | −2.245 | 0.0189 | −19.648 | conserved membrane protein of unknown function | S | Function unknown |
| Ent638_2302 | 3.151 | 0.0753 | 4.113 | oligopeptide transporter subunit; periplasmic-binding component of ABC superfamily | E | Amino acid transport and metabolism |
| Ent638_2303 | −2.254 | 0.0545 | −5.217 | conserved membrane protein of unknown function | S | Function unknown |
| Ent638_2306 | −2.221 | 0.0312 | −8.509 | global nucleic acid-binding transcriptional dual regulator H—NS | R | General function prediction only |
| Ent638_2313 | 3.051 | 0.199 | 2.167 | molybdenum-cofactor-assembly chaperone subunit (delta subunit) of nitrate reductase 1 | O | Posttranslational modification, protein turnover, chaperones |
| Ent638_2314 | 6.367 | 0.0415 | 6.486 | nitrate reductase 1, beta (Fe—S) subunit | C | Energy production and conversion |
| Ent638_2315 | 7.849 | 0.0258 | 11.405 | nitrate reductase 1, alpha subunit | C | Energy production and conversion |
| Ent638_2387 | 2.074 | 0.0294 | 9.374 | mannose-specific enzyme IIC component of PTS | G | Carbohydrate transport and metabolism |
| Ent638_2465 | 2.693 | 0.0548 | 5.199 | purine-binding chemotaxis protein | N; T | Cell motility; Signal transduction mechanisms |
| Ent638_2466 | 3.068 | 0.13 | 2.89 | fused chemotactic sensory histidine kinase in two-component regulatory system with CheB and CheY | T | Signal transduction mechanisms |
| Ent638_2497 | −2.021 | 0.0643 | −4.597 | Cold shock-like protein cspB (CSP-B) | K | Transcription |

TABLE S4-continued

| | Microarrays | | | | | |
|---|---|---|---|---|---|---|
| SEQ_ID_s | Fold Change (Rich/ Poor) | p value (FDR) | T statistic | FUNCTION | COGclassID | ClassDescription |
| Ent638_2502 | −2.125 | 0.0174 | −28.928 | conserved protein of unknown function | S | Function unknown |
| Ent638_2508 | 2.655 | 0.0579 | 4.969 | putative regulator of FliA activity | T | Signal transduction mechanisms |
| Ent638_2509 | 2.86 | 0.13 | 2.882 | RNA polymerase, sigma 28 (sigma F) factor | J | Translation, ribosomal structure and biogenesis |
| Ent638_2522 | 6.843 | 0.0198 | 18.732 | Flagellar filament structural protein (flagellin) | N; T | Cell motility; Signal transduction mechanisms |
| Ent638_2523 | 5.717 | 0.0572 | 5.012 | Flagellar filament capping protein | N | Cell motility |
| Ent638_2524 | 3.188 | 0.0406 | 6.71 | flagellar protein potentiates polymerization | N; O; U | Cell motility; Posttranslational modification, protein turnover, chaperones; Intracellular trafficking, secretion, and vesicular transport |
| Ent638_2533 | 2.468 | 0.0388 | 6.904 | flagellar protein | N; O; U | Cell motility; Posttranslational modification, protein turnover, chaperones; Intracellular trafficking, secretion, and vesicular transport |
| Ent638_2534 | 2.802 | 0.0365 | 7.502 | Flagellar hook-length control protein | C; N | Energy production and conversion; Cell motility |
| Ent638_2542 | −3.17 | 0.0476 | −5.778 | DNA-binding transcriptional activator, co-regulator with RcsB | K; T | Transcription; Signal transduction mechanisms |
| Ent638_2543 | −2.171 | 0.0152 | −27.401 | conserved protein of unknown function | S | Function unknown |
| Ent638_2579 | −2.28 | 0.0234 | −14.287 | Putative colicin | N; T; U | Cell motility; Signal transduction mechanisms; Intracellular trafficking, secretion, and vesicular transport |
| Ent638_2610 | −2.258 | 0.0263 | −10.572 | putative S lysis protein; Qin prophage | — | — |
| Ent638_2626 | −2.122 | 0.068 | −4.409 | Phage integrase family protein | L | Replication, recombination and repair |
| Ent638_2651 | −2.429 | 0.0329 | −8.064 | dTDP-4-deoxyrhamnose-3,5-epimerase | M | Cell wall/membrane/envelope biogenesis |
| Ent638_2750 | 4.192 | 0.0223 | 16.152 | methyl-galactoside transporter subunit; periplasmic-binding component of ABC superfamily | G | Carbohydrate transport and metabolism |
| Ent638_2795 | 2.662 | 0.031 | 8.549 | outer membrane porin protein C | M | Cell wall; membrane; envelope biogenesis |
| Ent638_2828 | 2.486 | 0.0284 | 9.737 | NADH:ubiquinone oxidoreductase, chain F | C | Energy production and conversion |

TABLE S4-continued

| | Microarrays | | | | | |
|---|---|---|---|---|---|---|
| SEQ_ID_s | Fold Change (Rich/Poor) | p value (FDR) | T statistic | FUNCTION | COGclassID | ClassDescription |
| Ent638_2837 | 2.01 | 0.0286 | 9.639 | putative phosphatase | R | General function prediction only |
| Ent638_2904 | −2.736 | 0.0284 | −9.812 | Phage transcriptional regulator, AlpA | K | Transcription |
| Ent638_2958 | 3.828 | 0.0373 | 7.411 | putative fused malic enzyme oxidoreductase; phosphotransacetylase | C | Energy production and conversion |
| Ent638_3059 | 4.692 | 0.0372 | 7.409 | anti-sigma factor | T | Signal transduction mechanisms |
| Ent638_3076 | 2.493 | 0.0411 | 6.566 | cold shock protein associated with 30S ribosomal subunit | J | Translation, ribosomal structure and biogenesis |
| Ent638_3088 | 3.12 | 0.0387 | 6.942 | tRNA (guanine-1-)-methyltransferase | J | Translation, ribosomal structure and biogenesis |
| Ent638_3112 | −2.019 | 0.0814 | −3.876 | conserved protein of unknown function | S | Function unknown |
| Ent638_3127 | −2.428 | 0.0452 | −5.987 | conserved protein of unknown function | S | Function unknown |
| Ent638_3133 | −2.01 | 0.08 | −3.929 | conserved protein of unknown function | S | Function unknown |
| Ent638_3249 | 2.827 | 0.043 | 6.214 | putative serine transporter | E | Amino acid transport and metabolism |
| Ent638_3322 | 2.185 | 0.0171 | 24.827 | glycine decarboxylase, PLP-dependent, subunit (protein P) of glycine cleavage complex | E | Amino acid transport and metabolism |
| Ent638_3323 | 2.857 | 0.101 | 3.402 | glycine cleavage complex lipoylprotein | E | Amino acid transport and metabolism |
| Ent638_3324 | 2.681 | 0.0931 | 3.563 | aminomethyltransferase, tetrahydrofolate-dependent, subunit (T protein) of glycine cleavage complex | E | Amino acid transport and metabolism |
| Ent638_3338 | 3.036 | 0.0172 | 25.473 | fructose-bisphosphate aldolase, class II | G | Carbohydrate transport and metabolism |
| Ent638_3339 | 3.055 | 0.0251 | 11.974 | phosphoglycerate kinase | G | Carbohydrate transport and metabolism |
| Ent638_3532 | 2.017 | 0.0435 | 6.165 | putative aldolase | G | Carbohydrate transport and metabolism |
| Ent638_3561 | 2.706 | 0.0174 | 32.635 | pyruvate formate-lyase 4/2-ketobutyrate formate-lyase | C | Energy production and conversion |
| Ent638_3562 | 2.214 | 0.0429 | 6.316 | propionate kinase/acetate kinase C, anaerobic | C | Energy production and conversion |
| Ent638_3563 | 4.426 | 0.00332 | 113.406 | L-threonine/L-serine transporter | E | Amino acid transport and metabolism |
| Ent638_3564 | 2.11 | 0.0248 | 11.174 | catabolic threonine dehydratase, PLP-dependent | E | Amino acid transport and metabolism |
| Ent638_3666 | 2.499 | 0.0331 | 8.017 | 50S ribosomal subunit protein L13 | J | Translation, ribosomal structure and biogenesis |
| Ent638_3671 | 3.291 | 0.0186 | 29.163 | malate dehydrogenase, NAD(P)-binding | C | Energy production and conversion |

TABLE S4-continued

| | Microarrays | | | | | |
|---|---|---|---|---|---|---|
| SEQ_ID_s | Fold Change (Rich/Poor) | p value (FDR) | T statistic | FUNCTION | COGclassID | ClassDescription |
| Ent638_3679 | −2.051 | 0.124 | −2.996 | membrane protein of efflux system | M | Cell wall/membrane/envelope biogenesis |
| Ent638_3686 | 2.015 | 0.025 | 11.894 | cell wall structural complex MreBCD transmembrane component MreC | M | Cell wall/membrane/envelope biogenesis |
| Ent638_3701 | −2.131 | 0.0253 | −11.29 | conserved protein of unknown function | S | Function unknown |
| Ent638_3722 | −2.133 | 0.048 | −5.712 | mechanosensitive channel | M | Cell wall/membrane/envelope biogenesis |
| Ent638_3723 | −2.564 | 0.0611 | −4.795 | conserved protein of unknown function | S | Function unknown |
| Ent638_3726 | 3.616 | 0.0248 | 11.127 | RNA polymerase, alpha subunit | K | Transcription |
| Ent638_3729 | 2.758 | 0.0306 | 8.691 | 30S ribosomal subunit protein S13 | J | Translation, ribosomal structure and biogenesis |
| Ent638_3730 | 4.562 | 0.0242 | 12.313 | 50S ribosomal subunit protein L36 | J | Translation, ribosomal structure and biogenesis |
| Ent638_3731 | 2.315 | 0.066 | 4.512 | preprotein translocase membrane subunit | U | Intracellular trafficking, secretion, and vesicular transport |
| Ent638_3732 | 2.484 | 0.0247 | 12.117 | 50S ribosomal subunit protein L15 | J | Translation, ribosomal structure and biogenesis |
| Ent638_3733 | 2.832 | 0.0307 | 8.659 | 50S ribosomal subunit protein L30 | J | Translation, ribosomal structure and biogenesis |
| Ent638_3735 | 2.087 | 0.0483 | 5.676 | 50S ribosomal subunit protein L18 | J | Translation, ribosomal structure and biogenesis |
| Ent638_3736 | 2.371 | 0.0477 | 5.736 | 50S ribosomal subunit protein L6 | J | Translation, ribosomal structure and biogenesis |
| Ent638_3737 | 2.068 | 0.129 | 2.923 | 30S ribosomal subunit protein S8 | J | Translation, ribosomal structure and biogenesis |
| Ent638_3744 | 2.017 | 0.0632 | 4.657 | 50S ribosomal subunit protein L16 | J | Translation, ribosomal structure and biogenesis |
| Ent638_3745 | 3.16 | 0.0219 | 15.304 | 30S ribosomal subunit protein S3 | J | Translation, ribosomal structure and biogenesis |
| Ent638_3746 | 4.129 | 0.0198 | 17.793 | 50S ribosomal subunit protein L22 | J | Translation, ribosomal structure and biogenesis |
| Ent638_3747 | 4.589 | 0.0316 | 8.444 | 30S ribosomal subunit protein S19 | J | Translation, ribosomal structure and biogenesis |
| Ent638_3748 | 3.398 | 0.0248 | 13.648 | 50S ribosomal subunit protein L2 | J | Translation, ribosomal structure and biogenesis |

TABLE S4-continued

| | | | | Microarrays | | |
|---|---|---|---|---|---|---|
| SEQ_ID_s | Fold Change (Rich/Poor) | p value (FDR) | T statistic | FUNCTION | COGclassID | ClassDescription |
| Ent638_3749 | 2.993 | 0.0225 | 15.415 | 50S ribosomal subunit protein L23 | J | Translation, ribosomal structure and biogenesis |
| Ent638_3750 | 2.484 | 0.0316 | 8.39 | 50S ribosomal subunit protein L4 | J | Translation, ribosomal structure and biogenesis |
| Ent638_3751 | 2 | 0.0386 | 6.918 | 50S ribosomal subunit protein L3 | J | Translation, ribosomal structure and biogenesis |
| Ent638_3752 | 4.398 | 0.019 | 19.524 | 30S ribosomal subunit protein S10 | J | Translation, ribosomal structure and biogenesis |
| Ent638_3756 | 2.017 | 0.00832 | 57.878 | protein chain elongation factor EF-Tu (duplicate of tufA) | J | Translation, ribosomal structure and biogenesis |
| Ent638_3757 | 2.087 | 0.0324 | 8.231 | protein chain elongation factor EF-G, GTP-binding | J | Translation, ribosomal structure and biogenesis |
| Ent638_3816 | 5.186 | 0.0352 | 7.667 | phosphoenolpyruvate carboxykinase | C | Energy production and conversion |
| Ent638_3925 | 3.294 | 0.0696 | 4.326 | C4-dicarboxylic acid, orotate and citrate transporter | C | Energy production and conversion |
| Ent638_4010 | 2.24 | 0.0202 | 17.884 | DNA-binding transcriptional dual regulator | K | Transcription |
| Ent638_4063 | -2.339 | 0.0436 | -6.128 | superoxide dismutase, Mn | P | Inorganic ion transport and metabolism |
| Ent638_4128 | 4.463 | 0.0247 | 11.192 | F0 sector of membrane-bound ATP synthase, subunit b | C | Energy production and conversion |
| Ent638_4129 | 3.599 | 0.0188 | 34.113 | F1 sector of membrane-bound ATP synthase, delta subunit | C | Energy production and conversion |
| Ent638_4130 | 3.583 | 0.0231 | 14.582 | F1 sector of membrane-bound ATP synthase, alpha subunit | C | Energy production and conversion |
| Ent638_4131 | 2.8 | 0.0306 | 8.832 | F1 sector of membrane-bound ATP synthase, gamma subunit | C | Energy production and conversion |
| Ent638_4132 | 4.856 | 0.0176 | 21.153 | F1 sector of membrane-bound ATP synthase, beta subunit | C | Energy production and conversion |
| Ent638_4133 | 3.713 | 0.0506 | 5.526 | F1 sector of membrane-bound ATP synthase, epsilon subunit | C | Energy production and conversion |
| Ent638_4202 | -2.485 | 0.0305 | -8.972 | Putative two-component response regulator | T | Signal transduction mechanisms |
| Ent638_4204 | -2.712 | 0.0382 | -7.009 | Two component transcriptional regulator, LuxR family | T | Signal transduction mechanisms |
| Ent638_4205 | -2.202 | 0.0516 | -5.436 | conserved protein of unknown function | S | Function unknown |
| Ent638_4206 | -2.27 | 0.047 | -5.835 | Putative outer membrane autotransporter barrel domain precursor | U | Intracellular trafficking, secretion, and vesicular transport |

TABLE S4-continued

| | Microarrays | | | | | |
|---|---|---|---|---|---|---|
| SEQ_ID_s | Fold Change (Rich/Poor) | p value (FDR) | T statistic | FUNCTION | COGclassID | ClassDescription |
| Ent638_4214 | −2.019 | 0.0762 | −4.057 | Glutamine amidotransferase-like protein yfeJ | E | Amino acid transport and metabolism |
| Ent638_4215 | −2.55 | 0.0408 | −6.676 | Plasmid stabilization system, toxin of toxin-antitoxin (TA) system ParE | D | Cell cycle control, cell division, chromosome partitioning |
| Ent638_4228 | −2.516 | 0.0666 | −4.487 | fragment of toxin of the RelE-RelB toxin-antitoxin system; Qin prophage (part 2) | D | Cell cycle control, cell division, chromosome partitioning |
| Ent638_4244 | −2.09 | 0.0854 | −3.762 | stress-induced protein, ATP-binding protein | R | General function prediction only |
| Ent638_4249 | −2.253 | 0.0748 | −4.131 | Replication protein repA | L | Replication, recombination and repair |
| Ent638_4268 | −3.098 | 0.0248 | −11.941 | bifunctional antitoxin of the RelE-RelB toxin-antitoxin system and transcriptional repressor; Qin prophage | D | Cell cycle control, cell division, chromosome partitioning |
| Ent638_4280 | −2.424 | 0.0409 | −6.625 | Putative lytic transglycosylase, catalytic (lysozyme-like virulence factors) | — | — |
| Ent638_4281 | −2.236 | 0.0533 | −5.312 | Putative conjugative transfer: mating signal (TraM) | D | Cell cycle control, cell division, chromosome partitioning |
| Ent638_4282 | −2 | 0.0323 | −8.245 | Protein of unknown function | S | Function unknown |
| Ent638_4313 | −2.362 | 0.0418 | −6.422 | Protein of unknown function | S | Function unknown |
| Ent638_4319 | −2.086 | 0.0736 | −4.179 | Truncated transposase (Tn3) | — | — |
| ENT630192 | −2.306 | 0.156 | −2.566 | exported protein of unknown function | S | Function unknown |
| ENT630194 | −2.286 | 0.0556 | −5.129 | exported protein of unknown function | S | Function unknown |
| ENT631068 | −2.732 | 0.0248 | −11.061 | protein of unknown function | S | Function unknown |
| ENT631584 | −2.087 | 0.037 | −7.431 | Putative autotransporter protein (fragment) | U | Intracellular trafficking, secretion, and vesicular transport |
| ENT631894 | −2.007 | 0.0174 | −21.346 | Beta-lactam resistance protein | R | General function prediction only |
| ENT631979 | −2.11 | 0.0229 | −14.717 | Putative IS element (IS600-like) | — | — |
| ENT632480 | −2.222 | 0.0545 | −5.219 | hypothetical protein | S | Function unknown |
| ENT632671 | −2.25 | 0.0249 | −11.071 | Hypothetical protein of unknown function | S | Function unknown |
| ENT632695 | −2.206 | 0.0523 | −5.384 | protein of unknown function | S | Function unknown |
| ENT633422 | −2.194 | 0.0264 | −10.451 | protein of unknown function | S | Function unknown |
| ENT633863 | 2.227 | 0.068 | 4.407 | hypothetical protein | S | Function unknown |
| ENT63p0011 | −2.333 | 0.0795 | −3.948 | protein of unknown function | S | Function unknown |
| ENT63p0054 | −2.572 | 0.0796 | −3.945 | protein of unknown function | S | Function unknown |
| ENT63p0058 | −2.469 | 0.0637 | −4.628 | protein of unknown function | S | Function unknown |

TABLE S4-continued

Microarrays

| SEQ_ID_s | Fold Change (Rich/ Poor) | p value (FDR) | T statistic | FUNCTION | COGclassID | ClassDescription |
|---|---|---|---|---|---|---|
| ENT63p0066 | −2.112 | 0.0251 | −11.251 | protein of unknown function | S | Function unknown |
| ENT63p0067 | −2.132 | 0.0241 | −12.455 | Putative partial transposase IS3/IS407 family | — | — |
| ENT63p0070 | −2.3 | 0.0375 | −7.358 | protein of unknown function | S | Function unknown |

TABLE S-3

Transporter comparison Ent638

| | | Sprot568 | Ent638 | E. coli K12 | E. coli O157-H7 | E. carotovora SCRI1043 | K. pneumoniae MGH78578 | 342 |
|---|---|---|---|---|---|---|---|---|
| 1.A. α-Type channels | | | | | | | | |
| The Voltage-gated Ion Channel (VIC) Superfamily | 1.A.1 | 1 | 2 | 1 | 1 | 0 | 1 | 1 |
| The Major Intrinsic Protein (MIP) Family | 1.A.8 | 2 | 2 | 2 | 2 | 1 | 5 | 4 |
| The Ammonia Transporter Channel (Amt) Family | 1.A.11 | 1 | 1 | 1 | 1 | 1 | 1 | 1 |
| The Large Conductance Mechanosensitive Ion Channel (MscL) Family | 1.A.22 | 1 | 1 | 1 | 1 | 1 | 1 | 1 |
| The Small Conductance Mechanosensitive Ion Channel (MscS) Family | 1.A.23 | 6 | 7 | 6 | 6 | 4 | 7 | 7 |
| The Urea Transporter (UT) Family | 1.A.28 | 0 | 0 | 0 | 0 | 0 | 0 | 0 |
| The CorA Metal Ion Transporter (MIT) Family | 1.A.35 | 4 | 2 | 2 | 3 | 2 | 3 | 3 |
| | total | 15 | 15 | 13 | 14 | 9 | 18 | 7 |
| 2.A. Porters (uniporters, symporters, antiporters) | | | | | | | | |
| The Major Facilitator Superfamily (MFS) | 2.A.1 | 114 | 81 | 70 | 76 | 64 | 119 | 128 |
| The Glycoside-Pentoside-Hexuronide (GPH):Cation Symporter Family | 2.A.2 | 1 | 5 | 6 | 6 | 3 | 8 | 9 |
| The Amino Acid-Polyamine-Organocation (APC) Family | 2.A.3 | 21 | 12 | 22 | 21 | 11 | 20 | 22 |
| The Cation Diffusion Facilitator (CDF) Family | 2.A.4 | 3 | 2 | 2 | 2 | 2 | 5 | 5 |
| The Zinc (Zn2+)-Iron (Fe2+) Permease (ZIP) Family | 2.A.5 | 1 | 1 | 0 | 0 | 0 | 1 | 1 |
| The Resistance-Nodulation-Cell Division (RND) Superfamily | 2.A.6 | 14 | 14 | 9 | 12 | 9 | 14 | 15 |
| The Drug/Metabolite Transporter (DMT) Superfamily | 2.A.7 | 26 | 19 | 16 | 16 | 19 | 25 | 28 |
| The Gluconate:H+ Symporter (GntP) Family | 2.A.8 | 6 | 2 | 7 | 4 | 3 | 4 | 6 |
| The Cytochrome Oxidase Biogenesis (Oxa1) Family | 2.A.9 | 1 | 1 | 1 | 1 | 1 | 1 | 1 |
| The 2-Keto-3-Deoxygluconate Transporter (KDGT) Family | 2.A.10 | 0 | 1 | 1 | 1 | 1 | 1 | 1 |
| The Citrate-Mg2+:H+ (CitM) Citrate-Ca2+:H+ (CitH) Symporter (CitMHS) Family | 2.A.11 | 0 | 0 | 0 | 0 | 2 | 0 | 0 |
| The ATP:ADP Antiporter (AAA) Family | 2.A.12 | 0 | 0 | 0 | 0 | 0 | 0 | 0 |
| The C4-Dicarboxylate Uptake (Dcu) Family | 2.A.13 | 2 | 2 | 2 | 2 | 2 | 2 | 2 |
| The Lactate Permease (LctP) Family | 2.A.14 | 1 | 1 | 2 | 1 | 1 | 1 | 1 |
| The Betaine/Carnitine/Choline Transporter (BCCT) Family | 2.A.15 | 2 | 0 | 3 | 3 | 1 | 3 | 2 |
| The Tellurite-resistance/Dicarboxylate Transporter (TDT) Family | 2.A.16 | 1 | 1 | 1 | 1 | 0 | 1 | 1 |
| The Proton-dependent Oligopeptide Transporter (POT) Family | 2.A.17 | 4 | 2 | 4 | 4 | 1 | 6 | 5 |
| The Ca2+:Cation Antiporter (CaCA) Family | 2.A.19 | 2 | 2 | 2 | 2 | 2 | 2 | 2 |
| The Inorganic Phosphate Transporter (PiT) Family | 2.A.20 | 2 | 1 | 2 | 2 | 1 | 1 | 1 |
| The Solute:Sodium Symporter (SSS) Family | 2.A.21 | 4 | 3 | 4 | 4 | 4 | 4 | 3 |
| The Dicarboxylate/Amino Acid:Cation (Na+ or H+) Symporter (DAACS) Family | 2.A.23 | 4 | 5 | 3 | 5 | 6 | 5 | 5 |
| The 2-Hydroxycarboxylate Transporter (2-HCT) Family | 2.A.24 | 2 | 1 | 0 | 0 | 2 | 2 | 3 |
| The Alanine or Glycine:Cation Symporter (AGCS) Family | 2.A.25 | 1 | 1 | 1 | 1 | 0 | 1 | 1 |
| The Branched Chain Amino Acid:Cation Symporter (LIVCS) Family | 2.A.26 | 2 | 1 | 1 | 1 | 1 | 1 | 1 |
| The Glutamate:Na+ Symporter (ESS) Family | 2.A.27 | 1 | 0 | 1 | 1 | 0 | 1 | 1 |
| The Bile Acid:Na+ Symporter (BASS) Family | 2.A.28 | 3 | 2 | 1 | 1 | 2 | 2 | 2 |
| The NhaA Na+:H+ Antiporter (NhaA) Family | 2.A.33 | 1 | 1 | 1 | 1 | 1 | 2 | 1 |
| The NhaB Na+:H+ Antiporter (NhaB) Family | 2.A.34 | 1 | 1 | 1 | 1 | 1 | 1 | 1 |
| The NhaC Na:H Antiporter (NhaC) Family | 2.A.35 | 1 | 0 | 0 | 0 | 0 | 0 | 0 |
| The Monovalent Cation:Proton Antiporter-1 (CPA1) Family | 2.A.36 | 2 | 2 | 2 | 2 | 1 | 3 | 3 |
| The Monovalent Cation:Proton Antiporter-2 (CPA2) Family | 2.A.37 | 4 | 3 | 3 | 3 | 2 | 3 | 3 |
| The K+ Transporter (Trk) Family | 2.A.38 | 2 | 1 | 2 | 1 | 1 | 1 | 1 |
| The K Transporter (Trk) Family | 2.A.39 | 2 | 0 | 2 | 2 | 2 | 3 | 4 |

TABLE S-3-continued

Transporter comparison Ent638

| | | | E. coli | | | E. carotovora | K. pneumoniae | |
|---|---|---|---|---|---|---|---|---|
| | | Sprot568 | Ent638 | K12 | O157-H7 | SCRI1043 | MGH78578 | 342 |
| The Nucleobase:Cation Symporter-2 (NCS2) Family | 2.A.40 | 6 | 5 | 10 | 11 | 4 | 7 | 7 |
| The Concentrative Nucleoside Transporter (CNT) Family | 2.A.41 | 4 | 2 | 3 | 3 | 3 | 3 | 2 |
| The Hydroxy/Aromatic Amino Acid Permease (HAAAP) Family | 2.A.42 | 5 | 5 | 8 | 8 | 3 | 7 | 7 |
| The Formate-Nitrite Transporter (FNT) Family | 2.A.44 | 3 | 3 | 4 | 4 | 2 | 2 | 2 |
| The Arsenite-Antimonite (ArsB) Efflux Family | 2.A.45 | 1 | 1 | 2 | 1 | 1 | 2 | 2 |
| The Benzoate:H+ Symporter (BenE) Family | 2.A.46 | 1 | 1 | 1 | 1 | 1 | 1 | 1 |
| The Divalent Anion:Na+ Symporter (DASS) Family | 2.A.47 | 4 | 4 | 5 | 5 | 4 | 6 | 8 |
| The Chloride Carrier/Channel (ClC) Family | 2.A.49 | 3 | 3 | 3 | 3 | 0 | 4 | 4 |
| The Chromate Ion Transporter (CHR) Family | 2.A.51 | 2 | 0 | 0 | 0 | 0 | 1 | 1 |
| The Ni2+—Co2+ Transporter (NiCoT) Family | 2.A.52 | 2 | 3 | 0 | 0 | 1 | 3 | 3 |
| The Sulfate Permease (SulP) Family | 2.A.53 | 4 | 2 | 1 | 1 | 2 | 4 | 3 |
| The Metal Ion (Mn2+-iron) Transporter (Nramp) Family | 2.A.55 | 2 | 1 | 1 | 1 | 1 | 1 | 2 |
| The Tripartite ATP-independent Periplasmic Transporter (TRAP-T) Family | 2.A.56 | 5 | 4 | 3 | 0 | 3 | 0 | 0 |
| The Phosphate:Na+ Symporter (PNaS) Family | 2.A.58 | 1 | 1 | 1 | 1 | 1 | 1 | 2 |
| The Arsenical Resistance-3 (ACR3) Family | 2.A.59 | 0 | 0 | 0 | 0 | 0 | 0 | 0 |
| The C4-dicarboxylate Uptake C (DcuC) Family | 2.A.61 | 1 | 2 | 2 | 2 | 1 | 1 | 1 |
| The Monovalent Cation (K+ or Na+):Proton Antiporter-3 (CPA3) Family | 2.A.63 | 0 | 0 | 0 | 0 | 0 | 0 | 0 |
| The Twin Arginine Targeting (Tat) Family | 2.A.64 | 4 | 4 | 4 | 4 | 4 | 4 | 4 |
| The Multidrug/Oligosaccharidyl-lipid/Polysaccharide (MOP) Flippase Superfamily | 2.A.66 | 9 | 8 | 8 | 8 | 5 | 6 | 4 |
| The Oligopeptide Transporter (OPT) Family | 2.A.67 | 1 | 0 | 0 | 0 | 0 | 0 | 0 |
| The p-Aminobenzoyl-glutamate Transporter (AbgT) Family | 2.A.68 | 1 | 1 | 1 | 2 | 0 | 1 | 1 |
| The Auxin Efflux Carrier (AEC) Family | 2.A.69 | 1 | 1 | 1 | 1 | 2 | 1 | 3 |
| The Malonate:Na+ Symporter (MSS) Family | 2.A.70 | 0 | 0 | 0 | 0 | 0 | 0 | 0 |
| The K+ Uptake Permease (KUP) Family | 2.A.72 | 2 | 1 | 1 | 1 | 1 | 1 | 1 |
| The Short Chain Fatty Acid Uptake (AtoE) Family | 2.A.73 | 0 | 0 | 1 | 0 | 0 | 0 | 0 |
| The L-Lysine Exporter (LysE) Family | 2.A.75 | 1 | 1 | 1 | 1 | 1 | 1 | 1 |
| The Resistance to Homoserine/Threonine (RhtB) Family | 2.A.76 | 9 | 4 | 5 | 5 | 11 | 7 | 9 |
| The Branched Chain Amino Acid Exporter (LIV-E) Family | 2.A.78 | 1 | 2 | 1 | 1 | 2 | 3 | 2 |
| The Threonine/Serine Exporter (ThrE) Family | 2.A.79 | 1 | 1 | 1 | 0 | 1 | 1 | 1 |
| The Tricarboxylate Transporter (TTT) Family | 2.A.80 | 3 | 0 | 0 | 0 | 0 | 0 | 0 |
| The Aspartate:Alanine Exchanger (AAE) Family | 2.A.81 | 2 | 2 | 1 | 0 | 2 | 2 | 2 |
| The Aromatic Acid Exporter (ArAE) Family | 2.A.85 | 5 | 5 | 3 | 3 | 0 | 6 | 8 |
| The Autoinducer-2 Exporter (AI-2E) Family (Formerly the PerM Family, TC #9.B.22) | 2.A.86 | 4 | 6 | 0 | 0 | 0 | 0 | 0 |
| The Vacuolar Iron Transporter (VIT) Family | 2.A.89 | 0 | 0 | 0 | 0 | 0 | 0 | 0 |
| | total | 319 | 241 | 244 | 244 | 202 | 319 | 340 |
| 3.A. P—P-bond-hydrolysis-driven transporters | | | | | | | | |
| The ATP-binding Cassette (ABC) Superfamily | 3.A.1 | 354 | 295 | 210 | 239 | 358 | 386 | 422 |
| The H+- or Na+-translocating F-type, V-type and A-type ATPase (F-ATPase) Superfamily | 3.A.2 | 9 | 9 | 9 | 9 | 9 | 9 | 9 |
| The P-type ATPase (P-ATPase) Superfamily | 3.A.3 | 7 | 8 | 6 | 6 | 6 | 9 | 10 |
| The Arsenite-Antimonite (ArsAB) Efflux Family | 3.A.4 | 0 | 0 | 0 | 0 | 0 | 1 | 2 |
| The General Secretory Pathway (Sec) Family | 3.A.5 | 7 | 6 | 0 | 0 | 0 | 3 | 3 |
| The H+-translocating Pyrophosphatase (H+-PPase) Family | 3.A.10 | 0 | 0 | 0 | 0 | 0 | 0 | 0 |
| The Septal DNA Translocator (S-DNA-T) Family | 3.A.12 | 1 | 1 | 0 | 0 | 0 | 0 | 0 |
| | total | 378 | 319 | 225 | 254 | 373 | 408 | 446 |
| 4.A. Phosphotransfer-driven group translocators | | | | | | | | |
| | 4.A | 45 | 41 | 50 | 63 | 45 | 84 | 78 |
| 9.A. Recognized transporters of unknown biochemical mechanism | | | | | | | | |
| The MerTP Mercuric Ion (Hg2+) Permease (MerTP) Family | 9.A.2 | 0 | 0 | 0 | 0 | 0 | 0 | 0 |
| The YggT or Fanciful K+ Uptake-B (FkuB; YggT) Family | 9.A.4 | 1 | 1 | 0 | 0 | 0 | 0 | 0 |
| The Ferrous Iron Uptake (FeoB) Family | 9.A.8 | 1 | 2 | 1 | 1 | 0 | 1 | 1 |
| The Iron/Lead Transporter (ILT) Superfamily | 9.A.10 | 1 | 1 | 0 | 0 | 0 | 0 | 0 |
| The Iron/Lead Transporter (ILT) Superfamily | 9.A.18 | 0 | 1 | 1 | 1 | 0 | 1 | 1 |
| The Mg2 Transporter-E (MgtE) Family | 9.A.19 | 2 | 2 | 0 | 0 | 1 | 2 | 2 |
| The Ethanolamine Facilitator (EAF) Family | 9.A.28 | 1 | 0 | 0 | 0 | 0 | 0 | 0 |
| The Putative 4-Toluene Sulfonate Uptake Permease (TSUP) Family | 9.A.29 | 2 | 1 | 0 | 0 | 0 | 0 | 0 |
| The Tellurium Ion Resistance (TerC) Family | 9.A.30 | 4 | 4 | 0 | 0 | 0 | 0 | 0 |
| The Pyocin R2 Phage P2 Tail Fiber Protein (Pyocin R2) Family | 9.A.33 | 1 | 1 | 0 | 0 | 0 | 0 | 0 |

TABLE S-3-continued

Transporter comparison Ent638

| | | Sprot568 | *E. coli* Ent638 | K12 | O157-H7 | *E. carotovora* SCRI1043 | *K. pneumoniae* MGH78578 | 342 |
|---|---|---|---|---|---|---|---|---|
| The HlyC/CorC (HCC) Family | 9.A.40 | 4 | 2 | 0 | 0 | 0 | 0 | 0 |
| The Capsular Polysaccharide Exporter (CPS-E) Family | 9.A.41 | 0 | 0 | 0 | 0 | 0 | 0 | 0 |
| total | | 17 | 15 | 2 | 2 | 1 | 4 | 4 |
| TOTAL | | 774 | 631 | 534 | 577 | 630 | 833 | 885 |
| % | | 15.4 | 14.4 | 12.9 | 10.9 | 14.1 | 16.1 | 15.3 | sources:
(1) http://www.membranetransport.org/ and
(2) http://www.tcdb.org/

What is claimed is:

1. A method of increasing drought tolerance in a plant comprising
applying an endophytic composition to the plant in an amount effective for increasing drought tolerance in the plant, wherein the endophytic composition consists essentially of an isolated culture of Enterobacter sp. 638, and wherein the plant is selected from tomato, sunflower, tobacco, corn, cucumber, pea, radish, broccoli and spinach.

2. The method of claim 1, comprising applying the endophytic composition to a root, a shoot, a leaf, and/or a seed of the plant.

3. A method of increasing drought tolerance in an angiosperm comprising the steps of
applying an amount effective of an endoroot composition consisting essentially of an isolated culture of *Enterobacter* sp. 638 to the angiosperm to increase drought tolerance in the angiosperm; and
increasing the drought tolerance in the angiosperm, wherein the angiosperm is selected from tomato, sunflower, and tobacco.

4. The method of claim 3, further comprising applying the endoroot composition to a root, a shoot, a leaf, and/or a seed of the angiosperm.

5. A method of increasing drought tolerance in a plant comprising
applying an endophytic composition consists essentially of an isolated culture of *Enterobacter* sp. 638 to the plant in an amount effective for increasing acetoin concentration, 2,3-butanediol concentration or both to confer drought tolerance in the plant, wherein the plant is selected from tomato, sunflower, tobacco, corn, cucumber, pea, radish, broccoli and spinach.

* * * * *

UNITED STATES PATENT AND TRADEMARK OFFICE
CERTIFICATE OF CORRECTION

PATENT NO. : 10,645,934 B2  
APPLICATION NO. : 13/634135  
DATED : May 12, 2020  
INVENTOR(S) : Lee Newman et al.

Page 1 of 1

It is certified that error appears in the above-identified patent and that said Letters Patent is hereby corrected as shown below:

On the Title Page

Item (73) Assignee should read: BROOKHAVEN SCIENCE ASSOCIATES, LLC, Upton, NY

Signed and Sealed this
Twenty-eighth Day of July, 2020

Andrei Iancu
*Director of the United States Patent and Trademark Office*